United States Patent
Hein et al.

(10) Patent No.: US 8,927,736 B2
(45) Date of Patent: Jan. 6, 2015

(54) COPPER CATALYZED CYCLOADDITION OF ORGANIC AZIDES AND 1-HALOALKYNES

(75) Inventors: Jason E. Hein, La Jolla, CA (US); Jonathan C. Tripp, Westfield, NJ (US); Larissa Krasnova, San Diego, CA (US); K. Barry Sharpless, La Jolla, CA (US); Valery V. Fokin, Oceanside, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/389,987

(22) PCT Filed: Aug. 11, 2010

(86) PCT No.: PCT/US2010/045134
§ 371 (c)(1), (2), (4) Date: Feb. 10, 2012

(87) PCT Pub. No.: WO2011/019799
PCT Pub. Date: Feb. 17, 2011

(65) Prior Publication Data
US 2012/0142935 A1    Jun. 7, 2012

Related U.S. Application Data

(60) Provisional application No. 61/273,939, filed on Aug. 11, 2009.

(51) Int. Cl.
*C07D 403/02* (2006.01)
*B01J 31/18* (2006.01)
*B01J 23/72* (2006.01)
*C07D 249/06* (2006.01)
*C07D 311/12* (2006.01)
*C07D 405/04* (2006.01)

(52) U.S. Cl.
CPC .............. *B01J 31/1805* (2013.01); *B01J 23/72* (2013.01); *B01J 31/181* (2013.01); *C07D 249/06* (2013.01); *C07D 311/12* (2013.01); *C07D 405/04* (2013.01); *B01J 2531/16* (2013.01)
USPC ......................................................... 548/255

(58) Field of Classification Search
USPC ......................................................... 548/255
See application file for complete search history.

(56) References Cited

PUBLICATIONS

Seela, et al., Organic and Biomolecular Chemistry, 2008, vol. 6, pp. 1674-1687, scheme 2.*
Kuijpers, Brian H. Copper (I)-Mediated Synthesis of Trisubstituted 1,2,3-Triazoles. SYNLETT. 20 (2005) 3059-3062.*

* cited by examiner

*Primary Examiner* — Samantha Shterengarts
(74) *Attorney, Agent, or Firm* — Olson & Cepuritis, Ltd.

(57) ABSTRACT

This invention provides a method for preparing a 1,2,3-triazole compound comprising contacting an organic azide with a 2-substituted-1-haloalkyne, in the presence of a copper catalyst and a copper-coordinating ligand (preferably a tertiary amine) in a liquid reaction medium, thereby forming a 1,4,5-substituted-1,2,3-triazole compound including a halo substituent at the 5-position of the triazole, the organic portion of the organic azide at the 1-position of the triazole, and the substituent of the 1-iodoalkyne at the 4-position of the triazole. A method for preparing 1-iodoalkynes is also provided.

28 Claims, 12 Drawing Sheets

| Entry | Additive | equiv | 3 : 4 : 5[b] | Yield[%][c] |
|---|---|---|---|---|
| 1 | – | – | – | n.r. |
| 2 | TEA | 0.5 | 10 : 3 : 1 | 55 |
| 3 | TEA | 1 | 25 : 2 : 1 | 75 |
| 4 | TEA | 2 | 1 : 0 : 0 | 90 |
| 5 | DIPEA | 0.5 | 15 : 1 : 2 | 47 |
| 6 | DIPEA | 2 | 1 : 0 : 0 | 73 |
| 7 | 2,6-lutidine | 0.5 | 30 : 1 : 0 | 12 |
| 8 | TMEDA | 0.5 | 20 : 1 : 0 | 26 |
| 9 | L1 | 0.5 | 1 : 1 : 15 | 25 |
| 10 | L2 | 0.5 | – | n.r. |
| 11 | L3 | 0.05 | 1 : 0 : 0 | 60[d] |
| 12 | L4 | 0.05 | 1 : 0 : 0 | 93[d] |

[a] General reaction conditions: CuI (0.02 mmol) and ligand in THF (2 mL), 1 (0.4 mmol) 2 (0.4 mmol), room temperature, 6h. [b] Product ratio determined by HPLC-MS. [c] Isolated yield of 3. [d] Reaction time was 45 min.

| Solvent | TTTA (5 mol%) | | TEA (2 equiv) | |
|---|---|---|---|---|
| | Time [h] | Yield[%] | Time [h] | Yield[%] |
| THF | 1 | 93 | 6 | 90 |
| MeCN | 1 | 94 | 6 | 85 |
| DMF | 2 | 91 | 18 | 86 |
| Water | 2 | 85 | 6 | 76 |
| EtOH | 4 | 78 | 24 | 69 |
| DCM | 4 | 79 | 24 | 62 |
| toluene | 5 | 62 | 24 | 73 | a] General conditions: CuI (0.025 mmol) and ligand in solvent (5 mL), 1 (0.5 mmol) 2 (0.5 mmol), room temperature [b] Isolated yield of 3.

[a] General reaction conditions: azide (1 mmol), 1-iodoalkyne (1 mmol), CuI (0.05 mmol), TTTA (0.05 mmol), THF (5mL), room temperature, 2h, [b] Values in parentheses represent isolate yield, [c] Reaction time was 6 h, [d] Reaction was performed at 10 mmol scale.

One-pot, three-step synthesis of 1,4,5-triaryltriazoles. PMP = *p*-methoxyphenyl, *p*-Tol = *p*-methylphenyl

COPPER CATALYZED CYCLOADDITION OF ORGANIC AZIDES AND 1-HALOALKYNES

CROSS-REFERENCE TO RELATED APPLICATIONS

This application claims the benefit of U.S. Provisional Application Ser. No. 61/273,939, filed on Aug. 11, 2009, which is incorporated herein by reference in its entirety.

STATEMENT OF GOVERNMENT SUPPORT

This invention was made with government support under Contract Nos. GM028384, GM083658 and GM087620 awarded by the National Institutes of Health. The Government has certain rights in this invention.

FIELD OF THE INVENTION

This invention relates to methods for preparing 1,2,3-triazole compounds. More particularly, this invention relates to the use of copper-catalyzed cycloaddition reactions of organic azides and 1-haloalkynes for regioselectively preparing 1,2,3-triazole compounds.

SUMMARY OF THE INVENTION

The present invention provides a method for regioselectively preparing a 1,2,3-triazole compound. The method comprises contacting an organic azide with a 2-substituted-1-haloalkyne (e.g., a 1-iodoalkyne), in the presence of a copper catalyst (e.g., comprising a Cu(I) ion) and a copper-coordinating ligand such as an amine (preferably a tertiary amine ligand), a thiol or salt thereof, a sulfide, a disulfide, a thiophene, a thiazole, and a phosphine, in a liquid reaction medium. The azide and haloalkyne condense in a manner akin to a [3+2] cycloaddition reaction to afford a 1,4,5-substituted-1,2,3-triazole compound including a halo substituent at the 5-position of the triazole, the organic portion of the organic azide at the 1-position of the triazole, and the substituent of the 1-iodoalkyne at the 4-position of the triazole.

In another aspect, the present invention provides a method for preparing 1-iodoalkynes. The method comprises contacting a terminal alkyne with an electrophilic iodinating agent (e.g., an N-iodoamine such as N-iodomorpholine, an iodo amide such as N-iodosuccinimide, etc) in the presence of a cuprous ion (e.g., a catalytic amount of a cuprous ion) in an aprotic solvent (e.g., THF), to afford a 1-iodoalkyne. The reaction between the electrophilic iodinating agent and the terminal alkyne advantageously and surprisingly occurs in high yields at ambient room temperature. The cuprous ion can be provided by a Cu(I) salt or can be generated in situ from Cu(II) via reduction.

The cycloaddition methods of the present invention provide an unexpected advantage over previously described cycloaddition reactions of organic azides with terminal alkynes, in that the reaction with 1-haloalkynes (particularly 1-iodoalkynes) can be significantly more rapid than the reaction with a corresponding terminal alkyne (i.e., having a hydrogen in place of the iodo substituent). In addition, the triazole end product of the cycloaddition reaction includes a halo substituent in the 5-position of the triazole, providing a "handle" for subsequent reactions at the 5 position to introduce other functionality (e.g., an aryl group, a polyethylene glycol group, and the like).

BRIEF DESCRIPTION OF THE DRAWINGS

The invention comprises certain novel features hereinafter fully described, and illustrated in the accompanying drawings, it being understood that various changes in the details may be made without departing from the spirit, or sacrificing any of the advantages of the present invention.

DETAILED DESCRIPTION OF PREFERRED EMBODIMENTS

Figure 1:
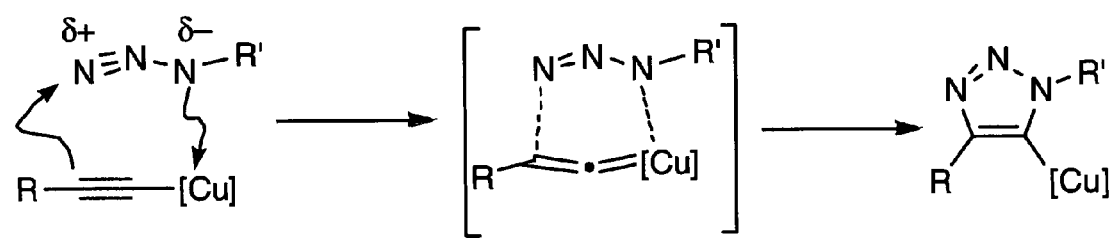
FIG. 1 illustrates a generalized reaction scheme for condensing an organic azide with a copper-acetylide.

The present invention provides a method for preparing a 1,2,3-triazole compound, which comprises, consists essentially of, or consists of contacting an organic azide with a 2-substituted-1-haloalkyne (e.g., a 1-iodoalkyne) in the presence of a copper catalyst and copper-coordinating ligand (preferably a tertiary amine ligand) in a liquid reaction medium. The azide and haloalkyne condense in a highly regioselective manner to afford a 1,4,5-substituted-1,2,3-triazole compound including a halo substituent at the 5-position of the triazole, the organic portion of the organic azide at the 1-position of the triazole, and the substituent of the 1-iodoalkyne at the 4-position of the triazole.

As used herein and is conventionally known in the art, the terms "alkyne" and "acetylene" and grammatical variations thereof, are used synonymously to refer to a compound including a carbon-carbon triple bond. The modifier "terminal" when used in conjunction with the terms "alkyne" or "acetylene" refers to compounds including a hydrogen at one terminus of a carbon-carbon triple bond and an organic substituent group at the other terminus.

In some preferred embodiments, the copper catalyst comprises, consists essentially of, or consists of a Cu(I) salt (e.g., cuprous sulfate or a cuprous halide salt such as cuprous bromide or cuprous iodide). If desired, the catalyst or a portion thereof can be generated in situ, e.g. by reduction of Cu(II) or by oxidation of Cu(0) to produce the catalytically active moiety. Suitable reducing agents for reducing Cu(II) and oxidizing agents for oxidizing Cu(0) are well known in the art. Some non-limiting examples of suitable reducing agents include ascorbates (e.g., ascorbic acid and/or ascorbate salts such as sodium ascorbate, and the like), thiols (e.g. glutathione, cysteine, dithiothreitol (DTT), and the like), metals (e.g., Cu(0) and the like), sulfite salts, thiosulfate salts, and hydroquinones. A preferred Cu(0) oxidizing agent is oxygen (e.g., from air). For example, the reaction between the azide and the haloalkyne can be preformed in the presence of copper metal under an oxygen-containing atmosphere (e.g., air) to generate the catalytically active copper species in situ. Alternatively, the reaction can be preformed with a Cu(II) salt in the presence of a reducing agent e.g., a thiol such as dithiothreitol (DTT), or an ascorbate salt. Thiols such as DTT and can also act as the copper-coordinating ligand in place of a tertiary amine, for example. m The copper-coordinating ligand can be any ligand containing a free electron pair capable of coordinating with copper. Ligands for copper are well known in the art. Preferably, the copper-coordinating ligand includes a nitrogen, sulfur, phosphorous, or oxygen atom or a combination of any of the foregoing, which has an affinity for copper. Examples of sulfur-containing copper-coordinating ligands include thiols and thiol salts such as thiophenol or a thiophenol salt, dithiothreitol (DTT) and the like, sulfides such as dimethylsulfide, diphenylsulfide and the like, disulfides such as dimethyldisulfide, diphenyldisulfide and the like, sulfur heterocycles such as thiophene (e.g., thiophen-2-carboxylic acid), thiazoles (e.g., thiazole 2-carboxylic acid), and the like. Examples of phosphorus-containing ligands include phosphines (e.g., triphenylphosphine, aminophosphines), and the like. Examples of nitrogen-containing copper-coordinating ligands include, nitrogen heterocycles (e.g., triazoles, tetrazole, ozazoles, pyridines and the like), and amines (e.g., tertiary amines). The copper-coordinating ligands can include any a combination of sulfur, nitrogen, phosphorus and oxygen-containing ligand groups if desired, e.g., triazole-substituted, thiophene-substituted, sulfide-substituted, oxazole-substituted, or disulfide-substituted tertiary amines, and the like.

Preferably, the copper-coordinating ligand is an amine ligand. The amine ligand can comprise any amine, but preferably comprises a tertiary amine. Trialkyl amines (e.g., $C_1$ to $C_{22}$ trialkyl amines such as triethylamine (TEA), diisopropylethylamine (DIPEA) and the like), and nitrogen heterocycle-substituted tertiary amines, e.g., triazole-substituted tertiary amines such as tris((1-tert-butyl-1H-1,2,3-triazolyl)methyl) amine (TTTA) and tris((1-benzyl-1H-1,2,3-triazolyl)methyl) amine (TBTA), are preferred in some embodiments. Other suitable triazole-substituted tertiary amines are disclosed in co-owned PCT Application No. PCT/US2008/010739, published as WO 2009/038685, which is incorporated herein by reference in its entirety.

The liquid reaction medium can comprise, consist essentially of, or consist of an aprotic organic solvent, and/or an alcohol and/or water. Generally, a suitable solvent will be selected based on the solubilities of the various reactants, catalysts, ligands, and/or products, as is well known in the art. Non-limiting examples of suitable types of aprotic solvents include ethers (e.g., tetrahydrofuran (THF), diethyl ether, dimethoxyethane (DME), and the like), amides (e.g., dimethylformamide, dimethylacetamide, N-methyl-pyrrolidinone, and the like, as well as alkyl substituted ureas such as N,N-dimethylpropyleneurea, and the like), nitriles (e.g., acetonitrile), hydrocarbons (e.g., toluene, xylenes, petroleum ethers, and the like), esters (e.g., ethyl acetate), ketones (e.g., acetone, methylethyl ketone (MEK), and the like), and halogenated hydrocarbons (e.g., a chlorinated hydrocarbon such as dichloromethane, and the like), as well as combinations of any of the foregoing. Non-limiting examples of suitable alcohols include methanol, ethanol, iso-propanol, propanol, butanol, iso-butanol, sec-butanol, tert-butanol, and the like, as well as combinations of any of the foregoing). If desired, the liquid medium can contain other materials and well known functional additives, such as pH buffers, surfactants (e.g., anionic surfactants such as sodium dodecyl sulfate (SDS), nonionic surfactants such as a polyethylene glycol, an ethoxylated alcohol, and the like; a cationic surfactant; or a zwitterionic surfactant), reducing agents, oxidizing agents, anti-foaming agents, dispersants, and the like, to adjust the chemical and physical properties of the medium, e.g., to aid in solubilization of the reactants, and the like.

In some embodiments, the organic azide is contacted with at least a stoichiometric amount of the 1-haloalkyne based on the molar amount of azide in the organic azide and the molar amount of alkyne in the 1-haloalkyne. In other embodiments, the organic azide is contacted with less than a stoichiometric amount of the 1-haloalkyne based on the molar amount of azide in the organic azide and the molar amount of alkyne in the 1-haloalkyne. In still other embodiments, the organic azide is contacted with greater than a stoichiometric amount of the 1-haloalkyne based on the molar amount of azide in the organic azide and the molar amount of alkyne in the 1-haloalkyne.

If desired, the method of the present invention can include the additional step of separating the 1,4,5-substituted-1,2,3-triazole compound from the copper-coordinating ligand and any copper-containing materials or additives that may be present. Such separation can be achieved through any suitable technique, including, without limitation, extraction, countercurrent extraction, precipitation, chromatography (e.g., thin layer chromatography (TLC), high performance liquid chromatography (HPLC), gas chromatography, preparative liquid chromatography, and the like), trituration, filtration, crystallization, or any combination of such techniques. Of course, one of ordinary skill in the chemical separations art will choose a separation technique that is compatible with the physical and chemical properties of the materials being separated, as is well known in the art. In addition, some preferred embodiments include the additional step of isolating the 1,4,5-substituted-1,2,3-triazole compound from the liquid reaction medium. Such isolation can be achieved, for example, by the separation techniques described above.

Yet other preferred embodiments of the present invention include contacting the 1,4,5-substituted-1,2,3-triazole compound with an arylboronic acid in the presence of a Pd(0) catalyst, to thereby replace the 5-halo substituent of the triazole with the aryl portion of the arylboronic acid. Alternatively, the method can include the additional step of contacting the 1,4,5-substituted-1,2,3-triazole compound with a reducing agent to replace the 5-halo substituent with a hydrogen.

The organic azide component of the present method can be any azide-substituted organic material, including, without limitation, any such organic azides that have been utilized in the well known copper-catalyzed azide-alkyne cycloaddition (CuAAC) reaction between terminal acetylenes and organic azides. Similarly, any terminal alkyne can be utilized in the present methods after conversion to a 1-haloalkyne (e.g., a 1-iodoalkyne), particularly any such alkynes that have been demonstrated to participate in the CuAAC reaction. The terminal alkynes can be conveniently converted to a 1-iodoalkynes by the method described herein. Reviews of the CuAAC reaction illustrating the broad range of organic azides and terminal alkynes that can be cyclized in the CuAAC reaction, include for example, Peng Wu and Valery V. Fokin, *Aldrichemica Acta,* 2007, 40(1): 7-17; John E. Moses and Adam D. Moorhouse, *Chemical Society Reviews,* 2007, 36 1249-1262; and Rolf Breinbauer and Maja Köhn, *ChemBioChem,* 2003, 4 1147-1149; as well as the references cited therein.

The breadth of organic moieties that can be included in the organic azides and 2-substituted 1-haloalkynes in the methods of the present invention is virtually without limit, and include, for example, simple and complex alkyl groups (including straight chain and branched alkyl, terpenes, steroids, fullerenes, and the like), aromatic groups (e.g., phenyl, naphthyl, anthryl, and the like), heterocyclic groups (including nitrogen, oxygen and/or sulfur-based heterocycles), heteroaromatic groups (including nitrogen, oxygen, and/or sulfur based heteroaromatic groups), carbohydrates (e.g., sugars, oligosaccharides, polysaccharides, and the like), amino acids, peptides, proteins, nucleic acids, polymeric materials (e.g., polyethylene glycols, polystyrenes, polyamides, polyacrylates, and the like) including biomolecules of all types, as well as materials bearing functional substituents such as alcohols, acids, thioacids, hydroxamic acids, amines, thiols, sulfides, disulfides, amides, ureas, esters, ethers, carbonates, halides, sulfonic acids, sulfoxides, sulfones, sulfonamides, sulfates, phosphates, phosphides, phosphonates, phosphonamides, and the like, as well as combinations of two or more of the foregoing.

In addition, the 2-substituent of the of the 1-haloalkyne can be a hydrogen, or can comprise a group bound to the 2-position of the 1-haloalkyne, e.g., via a carbon-carbon bond, a nitrogen-carbon bond, a chalcogen-carbon bond (e.g., oxygen, sulfur, selenium, tellurium), a silicon-carbon bond, a tin-carbon bond, or a phosphorous-carbon bond. In this manner, a wide variety of substituent types (e.g., proto, oxo, amino, silyl, stanyl, thio, seleno, telluro, and phospho groups), can be directly bound to 4-position of 1,2,3-triazoles by the methods of the present invention.

If desired, the organic azide and the 2-substituted-1-haloalkyne can be embodied in a single compound, in which case a polymeric triazole product can be obtained. Polytriazole materials have been reported to be useful as a thermal resistant polymer matrix for advanced composite materials (see, e.g., Wan et al. J. Appl. Poly. Sci., 2007; 104: 1038-1042). Polytriazoles reportedly have been prepared via [3+2] cycloaddition of bis-alkynes with bis-azides by Tang et al. U.S. Pat. Appl. Pub. No. 2008/0103273. Similar polytriazoles including 5-halo substituents on the triazole rings are accessible via the methods of the present invention, by utilizing bis-1-haloalkynes.

In addition, the 1-haloalkyne can be substituted with another alkyne moiety (e.g., a 1-haloalkyne, a terminal alkyne, or an internal alkyne), which can be utilized in a staged synthesis of bis-triazoles, utilizing the copper catalyzed azide 1-haloalkyne coupling reaction of the present invention, optionally in combination with the CuAAC reaction of terminal alkynes or the ruthenium catalyzed azide alkyne coupling of internal alkynes (e.g., as described in WO 2007/041451) to produce bis-triazoles that include a variety of different substituents on the two triazole rings of the coupled products.

The copper catalyzed cycloaddition of organic azides with 1-haloalkynes, as described herein, can be utilized advantageously in many areas of organic and bioorganic chemistry, including, for example, bioconjugation (see Moses and Moorhouse, supra), in which a biomolecule modified to include an azide or a 1-haloalkyne is reacted with an a 1-haloalkyne or an organic azide, respectively, to link the biomolecule to another organic material (e.g., a PEG group or a fluorescent dye). If desired the other organic material can itself be a biomolecule. Examples of biomolecules include, without limitation, proteins, enzymes, amino acids, cytokines (e.g., interferon-beta—"IFNβ"), chemokines, nucleic acids, carbohydrates, lipids, and complex conjugates thereof.

For example, a protein can be modified to include a 1-iodoalkyne, which can then be reacted with a polyethylene glycol (PEG)-substituted azide to introduce a PEG group onto the protein via a triazole linkage. Conversely, the protein can be modified to include an azide group, and the PEG compound can include the 1-iodoalkyne group. Such reactions can also be utilized to glycosylate a protein, e.g., by modifying a glycosyl compound with either a 1-haloalkyne or an azide and reacting with an appropriately substituted protein or peptide. The present method can also be useful for attaching various label and marker compounds (e.g., a fluorescent compound) onto a biomolecule, such as a protein. For example, since the halo substituent remains on the triazole product, the present methods can be used to introduce a radioactive iodine into a biomolecule, by using a radioiodine labeled 1-iodoalkyne as a reactant (i.e., one in which at least some of the iodine is $^{131}$I). In another example. a boron-10 containing group can be introduced onto a biomolecule or a PEG compound for use in neutron therapy for treating cancers.

Pegylation has been demonstrated to provide a number of advantages in the pharmaceutical field, including enhancing delivery of materials across the blood-brain barrier. For example, pegylation of interleukin-10 (IL-10, a potent glial regulator and analgesic for neurotrophic pain) and of brain derived neurotrophic factor (BDNF) have been reported to significantly improve the penetration distance of the protein into spinal cord tissue, while also increasing the biological half-like of the drug (see Soderquist et al., *J. Biomed. Mater. Res. A,* 2008 Dec. 1, online publication). The methods of the present invention provide an alternative method for pegylation of proteins. For example, an azido PEG compound can be condensed with a 1-haloalkyne-substituted protein or a pegylated 1-haloalkyne can be condensed with an azide-substituted protein as described herein.

Methods for introducing an azide group or an acetylene group onto a PEG compound or a protein are known in the art. For example, U.S. Pat. No. 4,041,041 describes a method for preparing terminal acetylene substituted amino acids, which can be converted to 1-iodoalkynes by the methods of the present invention. Introducing such an amino acid onto a protein (e.g., at the C-terminus, the N-terminus, or at a side chain) then provides a 1-iodoalkyne substituted protein for reaction with an azido-PEG compound. An added advantage of the present methods is that the PEG is introduced in conjunction with a triazole moiety, providing additional functionality in the pegylated protein.

Such bioconjugation reactions have been extensively investigated in the case of the CuAAC reaction. A particular advantage of the present methods is that the halo-substituent of the 1-haloalkyne remains on the triazole in the 5-position.

This halo substituent can be used to further functionalize the triazole in the 5-position. For example, an iodo substituent in the 5-position of the triazole can be replaced by another group, such as an aryl group (e.g., by Pd(0) catalyzed coupling with an arylboronic acid), a carboxyl group (e.g., by a metal-catalyzed carbonylation reaction), a sulfide group (e.g., by copper catalyzed nucleophillic substitution of the iodide by a thiol), and the like. Such new functional groups can themselves be further modified, as desired to include other functionality. Thus the 5-halo substituent provides a versatile handle for further modification of the 1,2,3-triazole compounds formed by the present methods.

In other applications, the methods of the present invention can be utilized to form triazole-functionalized dendrons and dendrimers, as well as polymeric materials, such functionalized adhesive coatings, as is known for the CuAAC reaction (see e.g., WO 2006/995046; WO 2006/012569; WO 2007/011967; WO 2007/012001, which are incorporated herein by reference in their entireties), but with the added advantage of including a useful iodo or halo substituent on the triazole ring.

In another aspect, the present invention provides a method for preparing 1-iodoalkynes. The method comprises contacting a terminal alkyne with an electrophilic iodinating agent (e.g., an N-iodoamine such as N-iodomorpholine, an iodo amide such as N-iodosuccinimide, etc.) in the presence of a cuprous catalyst such as cuprous iodide and the like in an aprotic solvent (e.g., THF or any other aprotic solvent, such as those described above in respect to the liquid reaction medium), to afford a 1-iodoalkyne. Inasmuch as Cu(II) can be readily reduced to cuprous form, Cu(II) salts can also serve as source of the cuprous catalyst. The reaction between the electrophilic iodinating agent and the terminal alkyne moiety advantageously and surprisingly occurs in high yields at ambient room temperature, as will be demonstrated in examples described herein. The catalyst preferably is present in a catalytic amount (e.g., in a less than stoichiometric amount relative to the alkyne moiety). Preferably the cuprous catalyst is present in an amount in the range of about 0.01 to about mol % based on the mole of alkyne moiety present (e.g., an amount in the range of about 1 to about 10 mol % or about 5 mol %).

Certain aspects and features of the present invention are provided herein in the following illustrative examples and discussion, with reference to the figures, schemes and tables in the attached drawings.

The present inventors have discovered that 1-haloalkynes, particularly 1-iodoalkynes, which are stable and readily accessible (vide infra) internal acetylenes, exhibit exceptional reactivity in the copper-catalyzed annulation reaction with organic azides. Indeed, their reactivity of 1-iodoalkynes toward azides in the copper catalyzed cycloaddition reaction appears to surpass that of terminal alkynes. As an added benefit, the products of the reaction, 5-iodo-1,2,3-triazoles, are versatile synthetic intermediates amenable for further functionalization. Although several syntheses of iodotriazoles are known, the reactions require stoichiometric amounts of copper catalysts and employ reactive electrophilic halogenating reagents (e.g., iodine chloride, N-bromosuccinimide). See e.g., (a) Y. M. Wu, J. Deng, Y. Li, Q. Y. Chen, *Synthesis* 2005, 1314; (b) L. Li, G. Zhang, A. Zhu, L. Zhang, *J. Org. Chem.* 2008, 73, 3630. In addition, some procedures require extended reaction times and generate mixtures of 5-H and 5-iodo-triazoles. See, e.g., (a) I. Perez-Castro, O. Caamano, F. Fernandez, M. D. Garcia, C. Lopez, E. De Clercq, *Org. Biomol. Chem.* 2007, 5, 3805; (b) Kuijpers et al. recently reported an elegant synthesis of 5-bromo-1,2,3-triazoles from 1-bromoalkynes, however reactions required 40 mol % Cu(I)/Cu(II), elevated temperature for 16-50 hours to reach completion; B. H. M. Kuijpers, G. C. T. Dijkmans, S. Groothuys, P. J. L. M. Quaedflieg, R. H. Blaauw, F. L. van Delft, F. P. J. T. Rutjes, *Synlett* 2005, 3059.

Disclosed herein is a general, rapid and operationally simple method for the chemo- and regioselective synthesis of 5-iodo-1,4,5-trisubstituted-1,2,3-triazoles from organic azides and iodoalkynes. The catalysis is preferably effected by Cu(I) iodide in the presence of a copper-coordinating ligand, such as an amine (preferably a tertiary amine). Other ligands such as dimethylsulfide, triphenylphosphine, thiophen-2-carboxylic acid, thiophenol, and diphenylsulfide were also examined and were found to facilitate copper-catalyzed azide/1-iodoalkyne cycloaddition reactions according to the present invention.

Figure 2:
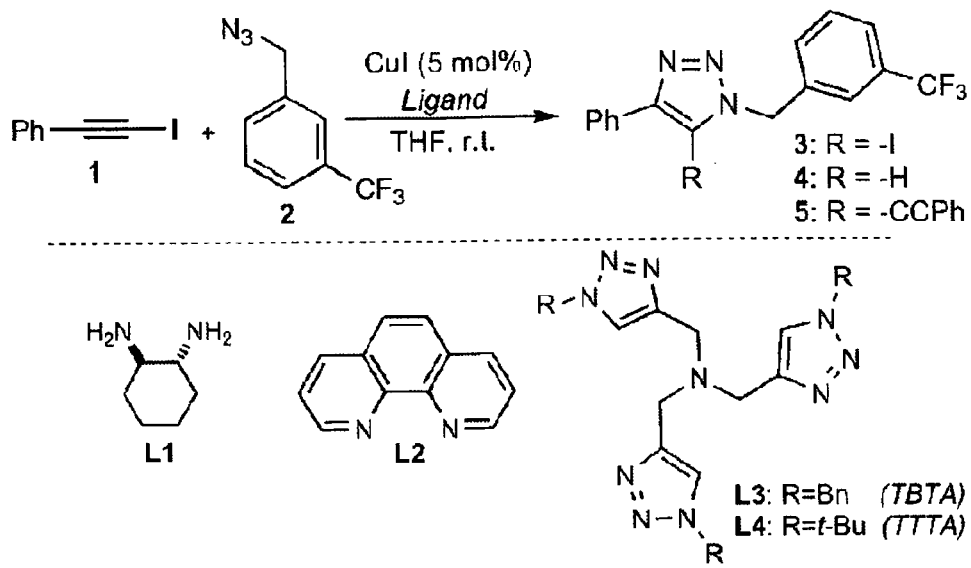
FIG. 2 provides a Table illustrating the effects of various amine ligands and other nitrogen-containing bases on the azide-haloalkyne cycloaddition.

An initial survey of experimental conditions, which included a broad array of Cu(I) and Cu(II) salts, solvents and ligands, revealed that the reaction of iodoalkyne 1 and azide 2 was catalyzed by Cu(I) iodide/triethylamine (TEA) in THF, affording 5-iodo-1,2,3-triazole 3 as the major product, along with varying amounts of 5-proto- and 5-alkynyl triazoles 4 and 5, respectively (see the Table 1, entry 2; FIG. 2). The regiochemistry of 3 was assigned by reducing the 5-iodo center to the 5-H-triazole, 4.

Inclusion of a copper-coordinating ligand such as an amine ligand is important as no reaction was observed when TEA was omitted (see Table 1, entry 1, in FIG. 2). Furthermore, the reaction displayed a sharp dependence on the quantity of TEA (Table 1, entries 1, 3 and 4; FIG. 2). Thus, 5-iodo-triazole 3 was generated as the sole product in excellent yield by simply using an excess (2 equiv.) of TEA. This trend extended to other tertiary amine ligands, although the desired 5-iodotriazole was obtained in lower yield (Table 1, entry 4 cf. 6, 8; FIG. 2).

The observed rate and chemoselectivity of the reaction were dependent on the nature of the amine ligand. For example, the efficiency of the reaction was markedly reduced and 5-alkynyl-triazole 5 was formed as the major product when TEA was replaced with 1,2-diamines (Table 1, entries 8 and 9; FIG. 2). Pyridines, such as 2,6-lutidine were less effective, while 1,10-phenanthroline was ineffective under the conditions employed (Table 1, entries 7 and 10; FIG. 2). By contrast, tris((1,2,3-triazolyl)methyl)amine ligands (see B. Gerard, J. Ryan, A. B. Beeler, J. A. Porco, Jr., *Tetrahedron* 2006, 62, 6405) were found to be highly efficient in this cycloaddition. Both tris((1-benzyl-1H-1,2,3-triazolyl)methyl)amine (TBTA) and its tert-butyl analog, tris((1-tert-butyl-1H-1,2,3-triazolyl)methyl)amine (TTTA) (Table 1, entries 11 and 12) provided 5-iodotriazole 3 as the exclusive product in excellent yield. In addition, these ligands markedly accelerated the reaction, reduce the time to completion from about 6 hours to about 45 minutes.

Figure 3:
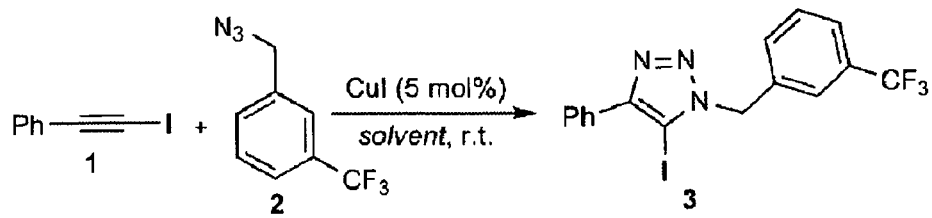
FIG. 3 provides a Table illustrating the effects of various solvents on the azide-haloalkyne cycloaddition reaction.

Based on these observations, TTTA has emerged as a preferred ligand for the rapid and chemoselective construction of 5-iodo-1,2,3 triazoles. It is noteworthy that both CuI-TTTA and CuI-TEA systems were found to be compatible with wide variety of solvents (Table 2; FIG. 3). While some solvents did have a significant effect on the reaction rate, the selectivity was not significantly affected, even when the reaction was performed in protic solvents (e.g., alcohols and water).

Figure 4:
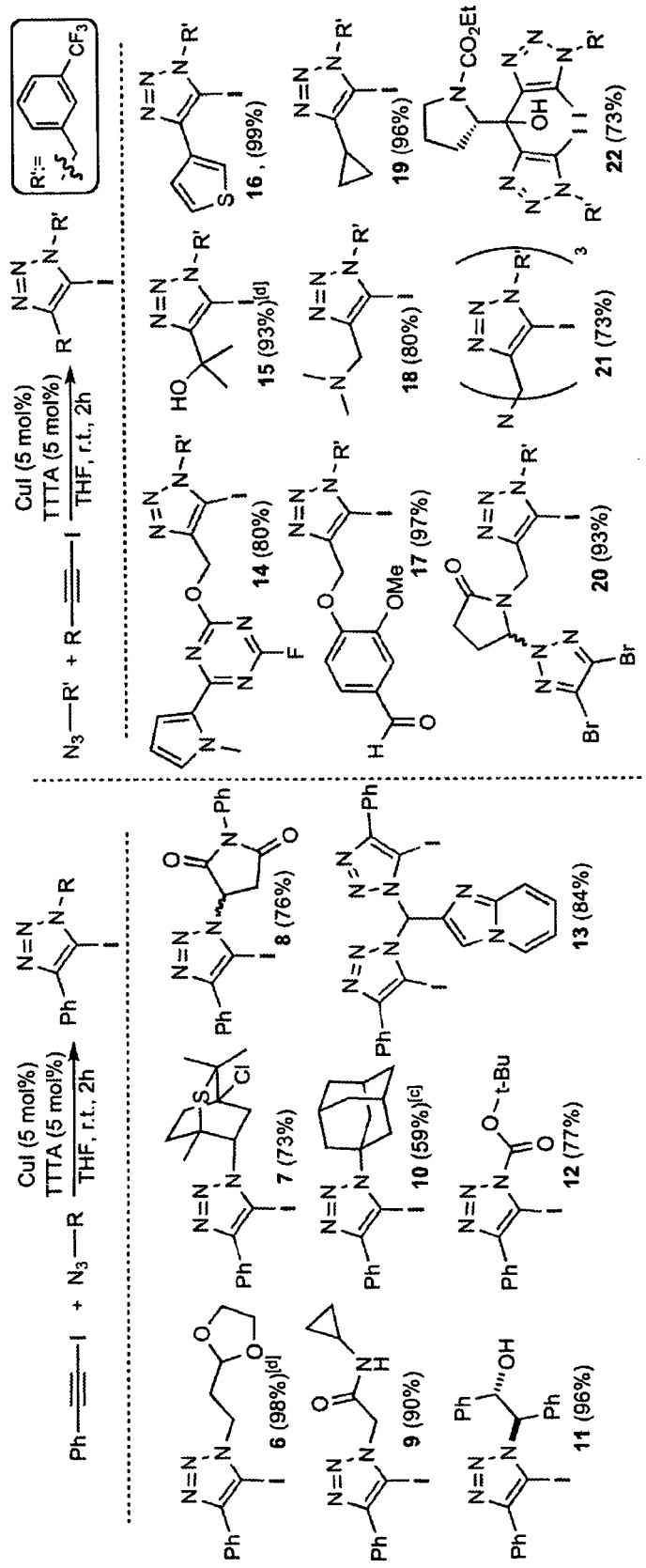
FIG. 4 provides examples of various 5-iodo-substituted 1,2,3-triazoles prepared according to the present invention.

The CuI-TTTA catalyst system was applied to a series of structurally and functionally diverse azides and 1-iodoalkynes (FIG. 4). In all cases, the 5-iodo-1,2,3-triazoles were obtained as the exclusive products. Due to the mild reaction conditions, high chemoselectivity, and low copper catalyst loading, reaction workup was usually as simple as trituration followed by filtration. As a result, this method is highly amenable to scale-up, and representative 5-iodotriazoles 6 and 15 were prepared in multigram quantities. In addition, the diverse array of functional groups tolerated by this annulation stands out as a particularly exceptional feature. Both sterically demanding (e.g., 10, 22) and functionally dense (e.g., 7, 17) substrates could be utilized. As such, the azide-iodoalkyne cycloaddition provides a highly orthogonal means of chemical ligation.

Figure 5:
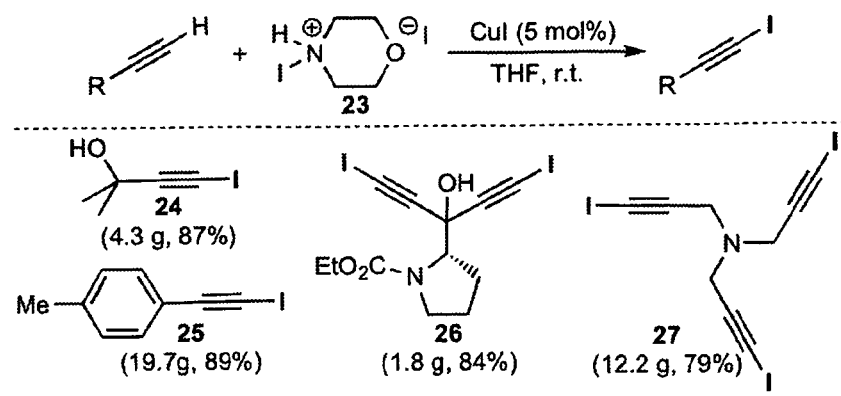
FIG. 5 illustrates various 1-iodoalkynes prepared according to the present invention.

The utility of this cycloaddition was enhanced through the development of a simple and highly efficient synthesis of 1-iodoalkynes from terminal alkynes (FIG. 5). Terminal alkynes were treated with N-iodomorpholine 23 (prepared per the procedure of Rice, U.S. Pat. No. 2,290,710), in the presence of CuI, to afford the corresponding 1-iodoakynes within 30 to 60 minutes. The obtained products could be isolated by simply passing the reaction mixture through a pad of silica gel or alumina, yielding the desired 1-iodoalkynes in good to excellent yield.

Figure 6:
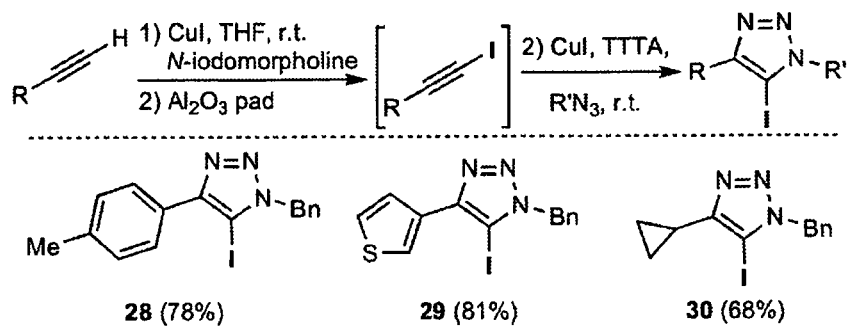
FIG. 6 illustrates in situ preparation of a 1-iodoalkyne and subsequent condensation of the iodoalkyne with an azide according to the methods of the present invention.

Given the speed and fidelity with which the 1-iodoalkynes can now be synthesized, a one-pot, two-stage protocol was developed (FIG. 6) for the preparation of 5-iodo-1,2,3-triazoles. The 1-iodoalkyne was partially purified via filtration through neutral alumina prior to the introduction of the azide component. Addition of electrophilic iodinating reagents (N-iodomorpholine, ICl, NIS, etc.) to a solution containing CuI-TTTA, the target azide and terminal alkyne rapidly gave the corresponding 1-iodoalkyne, but failed to promote the subsequent cycloaddition. This failure is likely due to the disruption of the catalytically active complex, either via oxidation of the metal or displacement/destruction of the ligand. This method afforded 5-iodotriazoles 28-30 with an efficiency comparable to that observed with the isolated 1-iodoalkynes.

Figure 7:
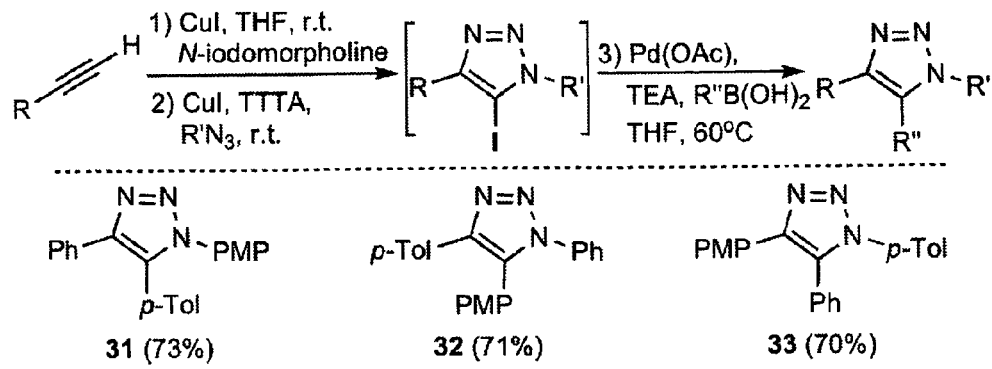
FIG. 7 illustrates reaction a procedure for forming 5-aryl-1,2-3-triazoles according to the present invention.

This sequence could be further extended to the synthesis of 1,4,5-triaryl-1,2,3-triazoles 31-33 (FIG. 7) by assembling the 5-iodotriazole and subsequently employing Pd(0)-catalyzed cross-coupling with an appropriate arylboronic acid. See e.g., J. Deng, Y.-M. Wu, Q.-Y. Chen, *Synthesis* 2005, 2730. This simple, step-wise construction obviates purification of any intermediates and simultaneously provides complete control over the placement of substituents around the 1,2,3-triazole core, allowing facile access to all regioisomeric permutations of triaryltriazoles 31-33. This achievement is notable, as a similar regiocontrolled synthesis would not be possible via thermal or ruthenium-catalyzed 1,3-dipolar cycloaddition due to the high degree of similarity between the aryl groups (phenyl, tolyl, and p-methoxyphenyl).

Figure 8:
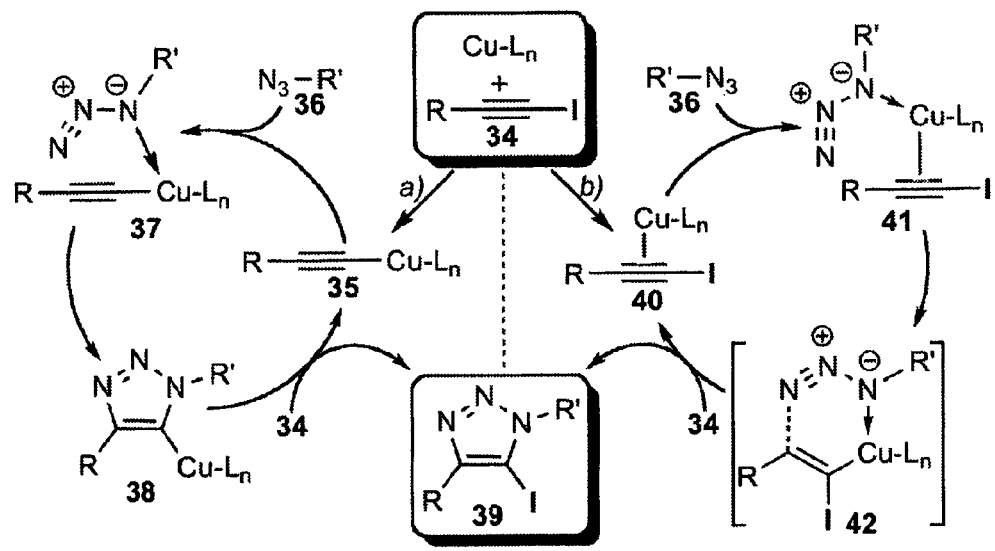
FIG. 8 schematically illustrates potential mechanisms for the present Cu(I)-catalyzed condensation of 1-haloalkynes with organic azides.

This newly discovered Cu(I)-catalyzed cycloaddition shares some similarities with the previously known CuAAC process (which utilizes terminal acetylenes); however, the modes of activation of iodo- and terminal alkynes by copper are distinctly different. Mechanistic proposals are outlined in FIG. 8. One possible pathway is similar to that proposed for the CuAAC (F. Himo, T. Lovell, R. Hilgraf, V. V. Rostovtsev, L. Noodleman, K. B. Sharpless, V. V. Fokin, *J. Am. Chem. Soc.* 2005, 127, 210) and involves the formation of the σ-acetylide complex 35 as the first key intermediate (FIG. 8, *a*). See e.g., P. Siemsen, R. C. Livingston, F. Diederich, *Angew. Chem. Int. Ed.* 2000, 39, 2632. Coordination of the azide via the proximal nitrogen is followed by the cyclization, yielding the cuprated triazoles 38. Cu(I) exchange via σ-bond metathesis with iodoalkyne 34 completes the cycle, liberating iodotriazole 39 and regenerating acetylide 35.

Alternatively, copper may activate the iodoalkyne via the formation of a π-complex intermediate (FIG. 8, *b*), which then engages the azide, producing complex 41. Cyclization then proceeds via a vinylidene-like transition state, 42, to give iodotriazole 39. A similar transition state has been proposed to explian the involvement of di-copper intermediates in the CuAAC reaction (a) M. Ahlquist, V. V. Fokin, *Organometallics* 2007, 26, 4389; b) B. F. Straub, *Chem. Comm.* 2007, 3868). The distinctive feature of this pathway is that the C—I bond is never severed and reformed during the catalysis.

Although a detailed examination of the mechanism has not been completed, pathway "b" is currently favored based on preliminary studies and the results from the reaction optimization experiments. The main argument in support of this hypothesis is the exclusive formation of the 5-iodotriazole even when the reaction is performed in protic solvents (Table 2; FIG. 3) or with the substrates containing acidic protons (FIG. 4, compounds 11, 15, 22). If pathway "a" were operational, the cuprated triazole intermediate 38 could be trapped with other electrophiles, including a proton, thereby producing a mixture of the 5-iodo and 5-prototriazoles. The absence of the latter products supports the hypothesis that pathway "a" is not dominant.

The new catalytic cycloaddition reaction enables rapid, controlled, and practical synthesis of 1,4,5-trisubstituted-1,2,3-triazoles. This reaction displays a broad substrate scope, excellent functional group compatibility, and remarkable solvent tolerance commensurate with the more familiar CuAAC reaction involving terminal alkynes. In addition to these immediate practical benefits, the unprecedented and exquisite reactivity of 1-iodoaceylenes disclosed here serves as a powerful tool to probe the mechanism of the copper-catalyzed transformations of alkynes, including the CuAAC reaction.

Figure 9:
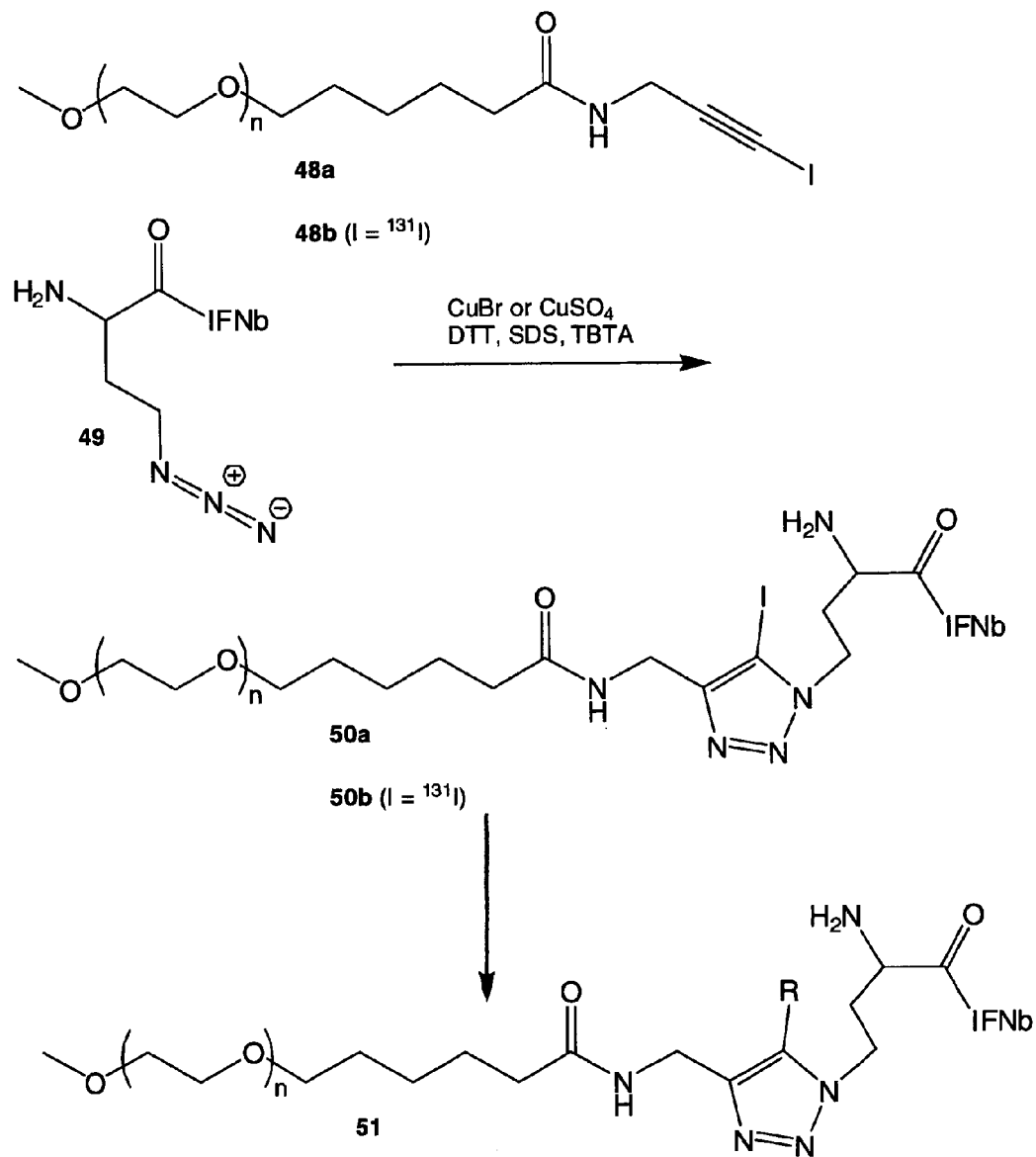
FIG. 9 provides a schematic representation of an illustrative application of the present methods in bioconjugation.

FIG. 9 provides a schematic illustration of a bioconjugation reaction utilizing the methods of the present invention. In FIG. 9, PEG-substituted 1-iodoalkyne 48a is reacted with azide-substituted IFNIβ 49 in the presence of CuBr or $CuSO_4$, dithiothreitol (DTT, a reducing agent), tris((1-benzyl-1H-1,2,3-triazolyl)methyl)amine (TBTA) as a ligand for copper, and optionally sodium docecyl sulfate (SDS) in an aqueous medium to afford a pegylated IFNβ derivative 50a having an iodo substituent in the 5-position of the triazole ring, which can be further functionalized to triazole 51 by conversion of the iodo substituent to another functional group (e.g., to introduce another PEG group, an aromatic group, a carbohydrate, a carboxylic acid, etc.). If a radioactive iodo group is introduced into PEG-substituted 1-iodoalkyne (e.g., $^{131}I$, as in 48b) then the resulting triazole 50b will be $^{131}I$ labeled, as well. Pegylation utilizing the iodotriazole linkage can provide an opportunity for additional pegylation if desired by replacing the iodo substituent.

In addition, the present methods can be utilized to prepare a number of different, useful materials of therapeutic or diagnostic use. For example, boron compounds have been used as a secondary radiation source in treatment of brain tumors (gliomas). See e.g., Barth et al, *J. Neuro-Oncology*, 1997; 33: 3-7. The boron compound (e.g., sulfhydryl borane $Na_2B_{12}H_{11}SH$ (BSH), p-dihydroxyborylphenylalanine (BPA), a boron-substituted polymer, a targeted boron-substituted antibody, and the like) is administered to a tumor (e.g., a glioma) and then irradiated, in situ, with neutrons. When a boron-10 atom in the boron compound absorbs a neutron, it undergoes fission to form lithium-7 and an energetic alpha particle. The high energy alpha particles formed from the fission reaction are highly effective at killing tumor cells.

Figure 10:
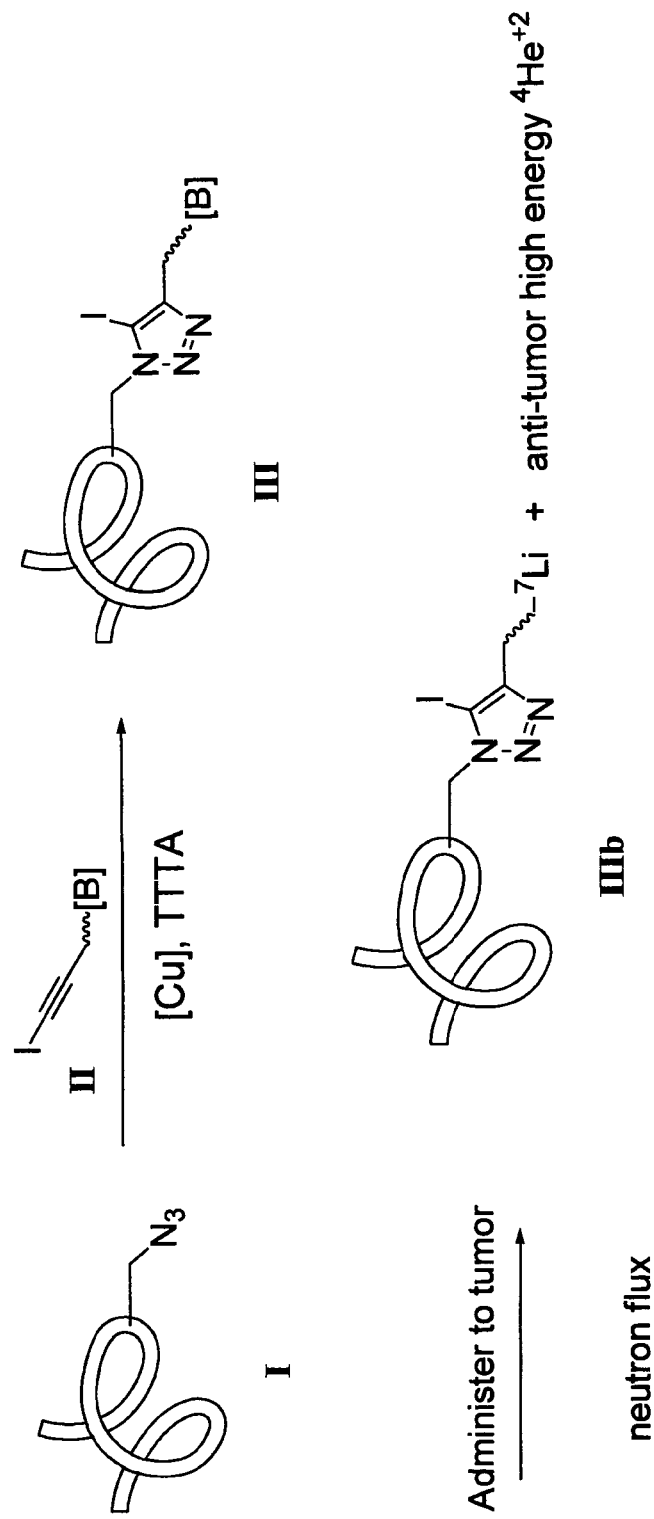
FIG. 10 provides a schematic illustration of one approach for appending a boron-10 containing material onto a targeting scaffold compound such as a biomolecule.

Tissue-targeted boron-10 materials can be useful in such cancer treatments. The methods of the present invention provide a general procedure for preparing targeted boron compounds. FIG. 10 provides a schematic illustration of one approach for appending a boron-10 containing material onto a targeting scaffold compound such as a biomolecule (e.g., a protein, an antibody, and the like) or a polymer (e.g., a polyethylene glycol group). In FIG. 10, a scaffold molecule (I) is coupled with a boron-substituted 1-iodoalkyne (II) in the presence of a copper catalyst and an amine ligand (e.g., TTTA) to form a triazole (III) that includes a boron-containing substituent in the 5-position of a 5-iodo-1,2,3-triazole moiety, and the scaffold group in the 1-position of the triazole. Targeted molecule (III) can then be administered to a tumor and irradiated with neutrons to release high energy alpha particles to attach the tumor cells. Alternatively, of course, the scaffold molecule can be substituted with a 1-iodoalkyne and the boron compound can be appended to an azide, such that the resulting boron-substituted platform molecule has the scaffold bound to the 4-position of the triazole and the boron-containing substituent bound to the 1-position of the triazole.

Figure 11:
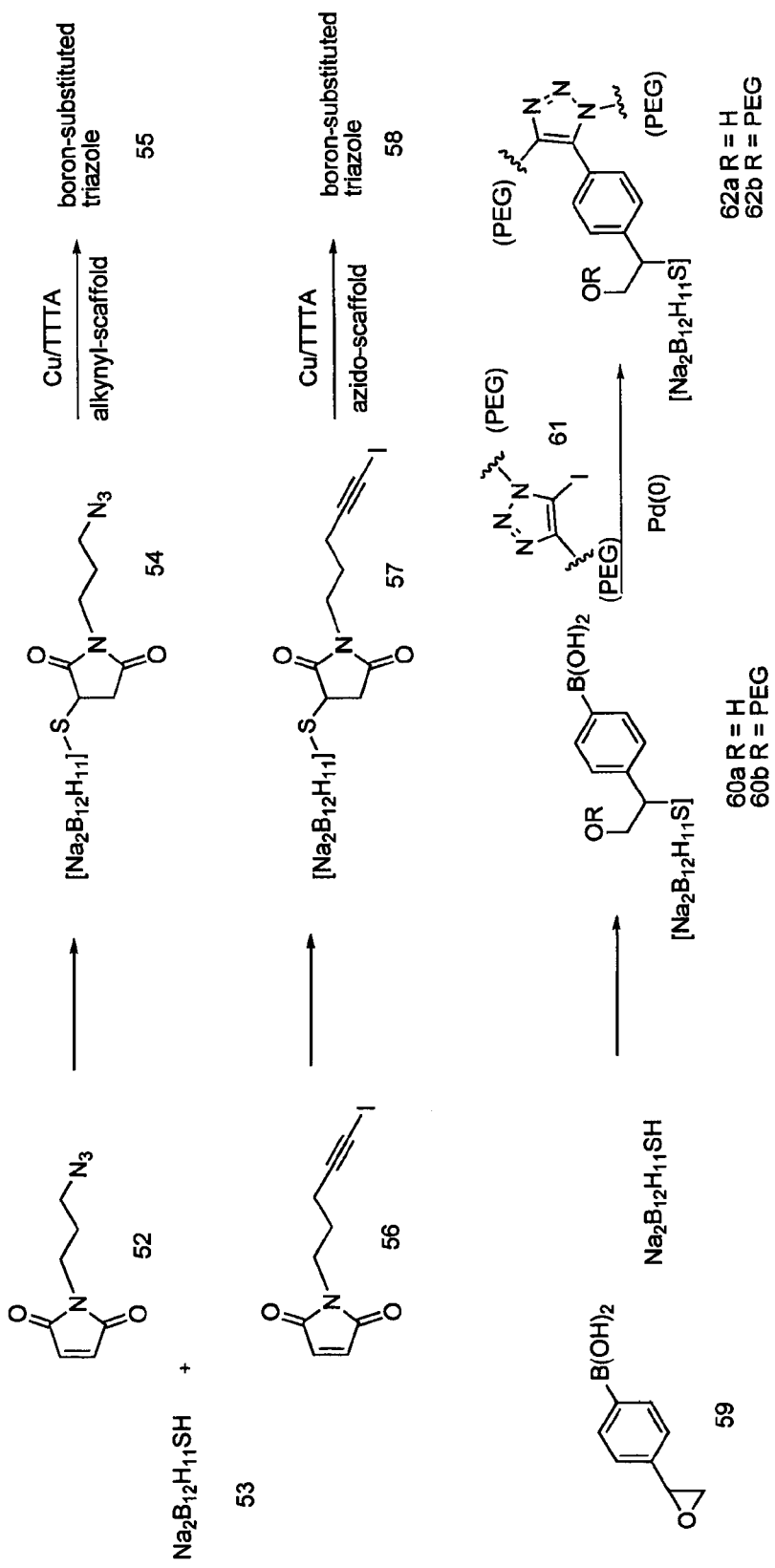
FIG. 11 provides examples of pegylation of borane compounds useful for neutron therapy for gliomas.

A PEG substituent can be used enhance transport of a boron compound across the blood-brain barrier, as has been observed for other pegylated therapeutic agents. Exemplary pegylated borane compounds useful for neutron therapy for gliomas can be prepared as shown in FIG. 11. In one embodiment, azide-substituted maleimide 52 is reacted with $Na_2B_{12}H_{11}SH$ to form borane-substituted succinimide 54, which can then be condensed with a pegylated 1-iodoalkyne according to the methods of the present invention to afford a borane-substituted pegylated triazole compound 55. Alternatively, 1-iodoalkyne-substituted maleimide compound 56 can be reacted with $Na_2B_{12}H_{11}SH$ to form borane-substituted 1-iodoalkyne 57, which can then be condensed with a pegylated azide to afford borane-substituted pegylated triazole compound 58.

In yet another alternative example, the borane moiety can be incorporated into a pegylated iodotriazole formed by the present methods by replacement of the iodo group. For example, as also shown in FIG. 11, epoxy-substituted phenylboronic acid 59 can be reacted with $Na_2B_{12}H_{11}SH$ to form borane-substituted phenylboronic acid 60a. Optionally, the hydroxyl group of 60a can be pegylated to form compound 60b. Pd(0) catalyzed coupling of boronic acid 60a with a pegylated 5-iodotriazole (61) formed by the methods of the present invention, then affords a pegylated borane compound 62a. Alternatively, pegylated boronic acid 60b can be coupled with an iodotriazole 61 (which also can be pegylated if desired) to form another useful type of pegylated borane, i.e., 62b.

Figure 12:
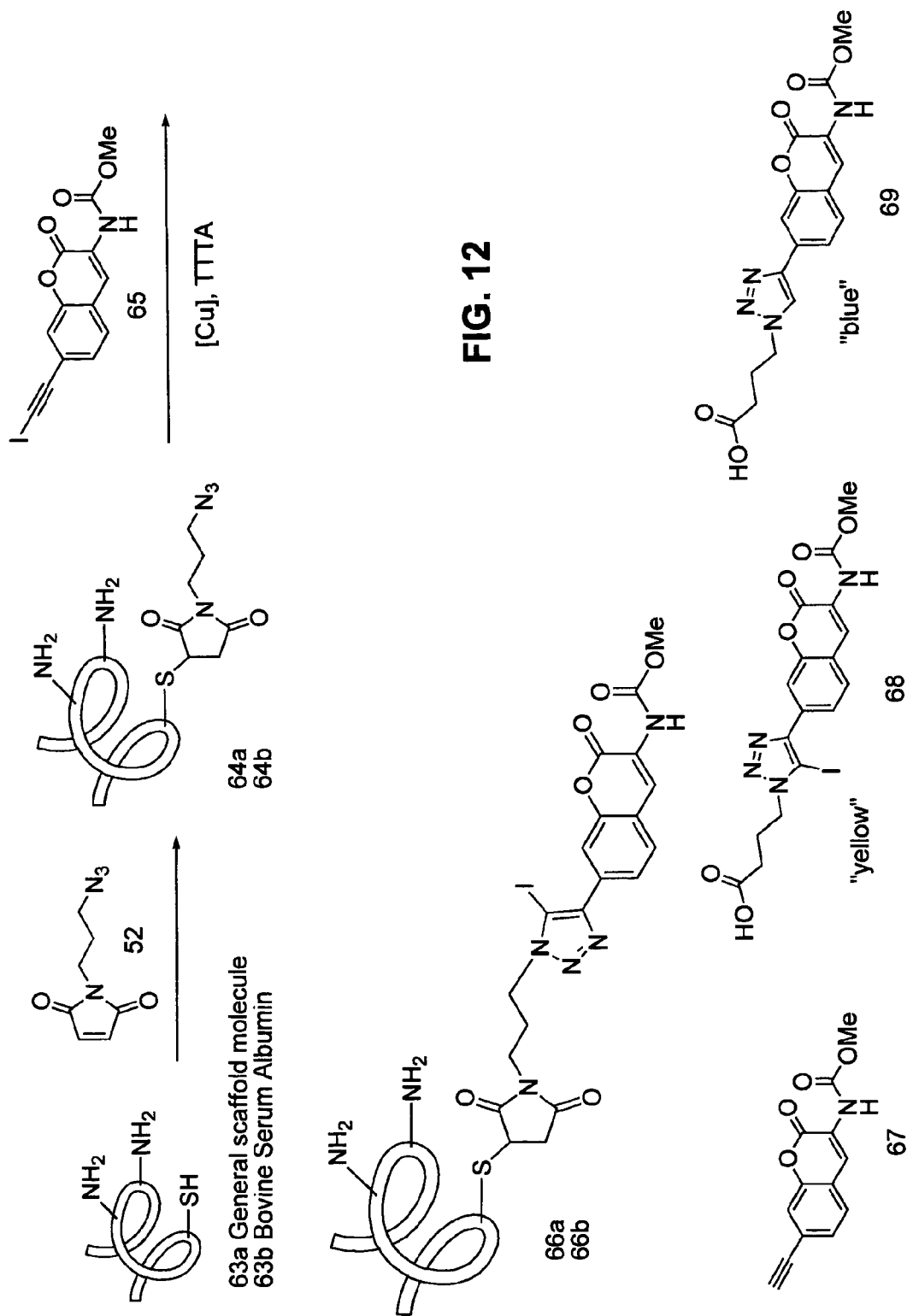
FIG. 12 provides an example of bioconjugation to introduce a fluorescent dye moiety according to the methods of the present invention, as well as examples of acetylene and triazole substituted coumarin compounds useful for bioconjugation reactions.

An example of bioconjugation to introduce a fluorescent dye moiety is shown in FIG. 12. A biomolecule scaffold 63 (e.g., a protein such as an antibody or antigen-binding fragment of an antibody, such as a $F(ab)_2$ fragment) can be condensed with azide-substituted maleimide 52 to provide an azido-substituted scaffold 64. Condensation of azide 64 with a 1-iodoalkyne-substituted coumarin dye 65 affords a biomolecule coupled to an iodo-triazole-substituted coumarin dye. In this manner, bovine serum albumin (BSA, the biomolecule scaffold compound) was coupled to coumarin 65 to form fluorescent labeled BSA 66b. Interestingly, coumarin 65 and its terminal alkyne precursor 67 are not fluorescent, but are fluorogenic when reacted with azides according to the present invention. Triazole compounds 68 and 69 fluoresce with a blue or yellow color, respectively.

Each of novel compounds 65, 67, 68, and 69 shown in FIG. 12, are useful materials for fluorescent labeling of biomolecules such as proteins. Accordingly, another aspect of the present invention provides fluorogenic alkyne-substituted coumarin compounds of the general Formula IV:

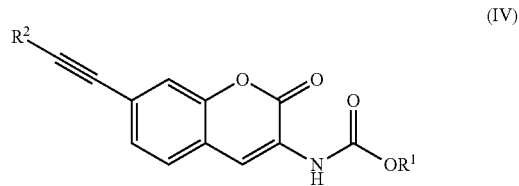

(IV)

wherein $R^1$ can be H, alkyl (e.g., $C_1$-$C_{20}$ alkyl such as methyl, ethyl, propyl, t-butyl, and the like), arylalkyl (e.g., $C_6$-$C_{14}$-aryl substituted $C_1$-$C_{20}$ alkyl such as benzyl, 2-phenylethyl, naphtylmethyl, and the like), aryl (e.g., $C_6$-$C_{14}$-aryl such as phenyl, naphthyl, and the like), alkylaryl (e.g., $C_1$-$C_{20}$ alkyl-substituted $C_6$-$C_{14}$-aryl such as tolyl, xylyl, nonylphenyl, 2-methylnaphthyl, and the like), heteroaryl (e.g., N, O, and/or S heterocyclic aromatic group such as pyridyl, phenanthryl, oxazolyl, thiazolyl, azolyl, furanyl, thiopheneyl, triazolyl, and the like), and a heterocyclic moiety (e.g., a N, O, and/or S heterocyclic group such as a cyclic amine, amide, urea, imide, sulfide, disulfide, sulfoxide, sulfone, ether, ester, carbonate, and the like), optionally including one or more substituents such as alcohols, acids, thioacids, hydroxamic acids, ureas, amines, thiols, sulfides, disulfides, sulfonic acids, sulfoxides, sulfones, sulfonamides, sulfates, esters, carbonates, ethers, halides, phosphates, phosphides, phosphonates, phosphonamides, and the like. $R^2$ can be I, or $R^1$.

In the case wherein $R^2$ is H, the terminal acetylene group can be coupled to an azide-substituted biomolecule scaffold via the CuAAC coupling reaction. When $R^2$ is I, the 1-iodoalkyne group can be coupled to an azide-substituted biomolecule scaffold via the methods of the present invention. When $R^2$ is other than H or I, the internal alkyne group can be coupled to an azide-substituted biomolecule scaffold via ruthenium catalyzed azide-alkyne coupling (see. e.g., WO 2007/041451, which is incorporated herein by reference in its entirety).

In yet another aspect, the present invention provides fluorescent triazole-substituted coumarin compounds of the general Formula V:

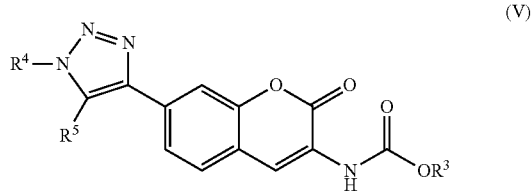

(V)

wherein $R^3$ can be H, alkyl (e.g., $C_1$-$C_{20}$ alkyl such as methyl, ethyl, propyl, t-butyl, and the like), arylalkyl (e.g., $C_6$-$C_{14}$-aryl substituted $C_1$-$C_{20}$ alkyl such as benzyl, 2-phenylethyl, naphtylmethyl, and the like), aryl (e.g., $C_6$-$C_{14}$-aryl such as phenyl, naphthyl, and the like), alkylaryl (e.g., $C_1$-$C_{20}$ alkyl-substituted $C_6$-$C_{14}$-aryl such as tolyl, xylyl, nonylphenyl, 2-methylnaphthyl, and the like), heteroaryl (e.g., N, O, and/or S heterocyclic aromatic group such as pyridyl, phenanthryl, oxazolyl, thiazolyl, azolyl, furanyl, thiopheneyl, triazolyl, and the like), and a heterocyclic moiety (e.g., a N, O, and/or S heterocyclic group such as a cyclic amine, amide, urea, imide, sulfide, disulfide, sulfoxide, sulfone, ether, ester, carbonate, and the like), optionally including one or more substituents such as alcohols, acids, thioacids, hydroxamic acids, ureas, amines, thiols, sulfides, disulfides, sulfonic acids, sulfoxides, sulfones, sulfonamides, sulfates, esters, carbonates, ethers, halides, phosphates, phosphides, phosphonates, phosphonamides, and the like. $R^4$ can be a biomolecule (e.g., a protein, a carbohydrate, a lipid, and the like), or $R^3$; and $R^5$ can be I, or $R^3$. The biomolecule can be selected from, for example, a protein, a carbohydrate, an amino acid, a lipid, and a nucleotide, a nucleoside, and a nucleic acid.

Figure 13:
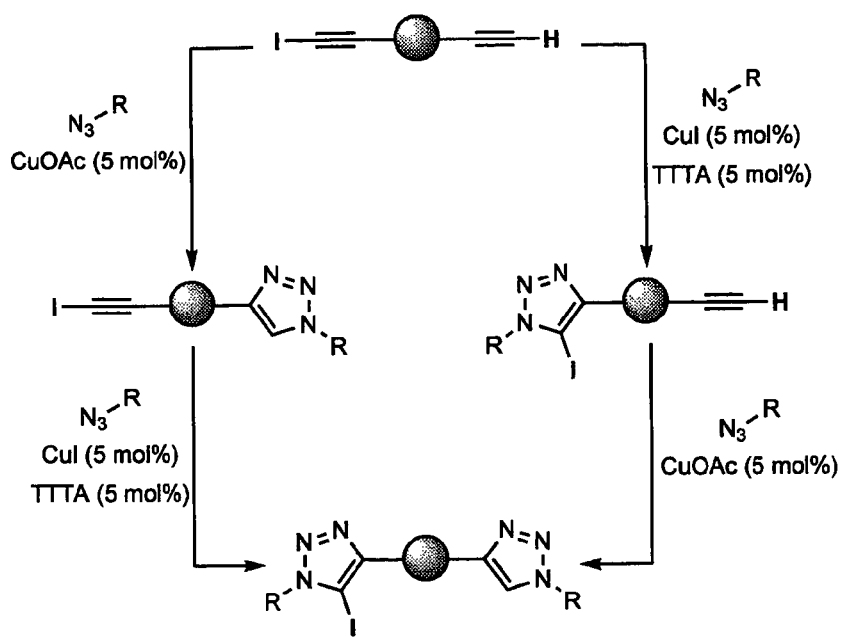
FIG. 13 provides a schematic example of a staged bis-triazole synthesis according to the methods of the present invention.
Figure 14:
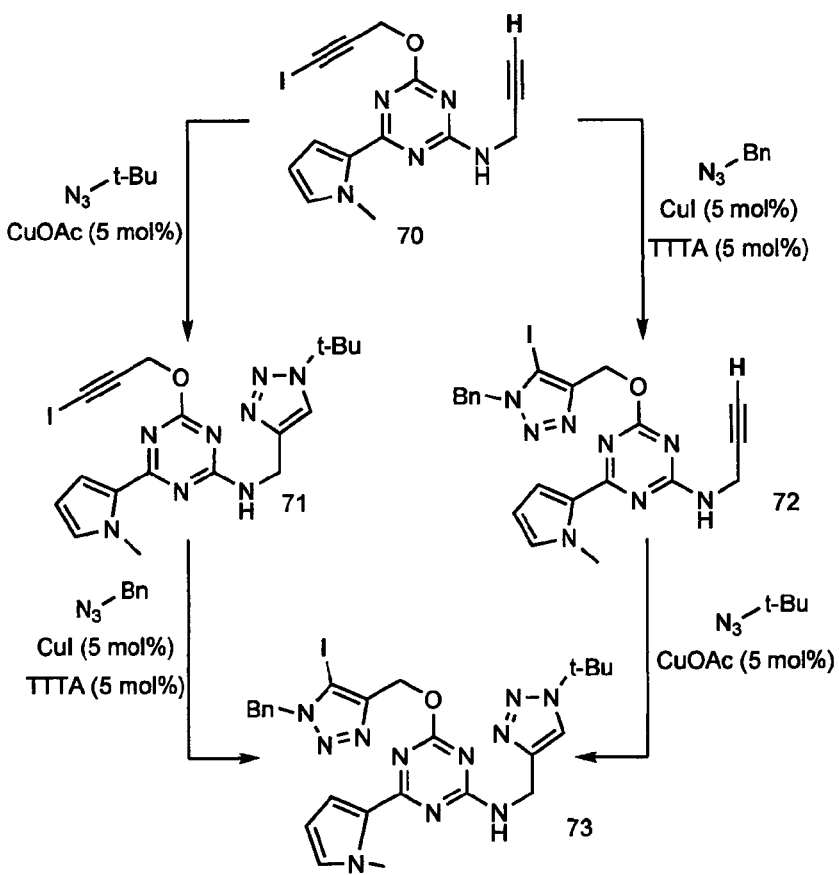
FIG. 14 provides a specific example of a staged bis-triazole synthesis according to the methods of the present invention.

Optionally, the 2-substituted 1-haloalkyne utilized in the methods of the present invention can include another 1-halo, terminal, or internal alkyne substituent. In such cases the haloalkyne moiety or moieties can be reacted with an azide according to the methods of the present invention, while a terminal alkyne substituent can be reacted with an azide via the CuAAC reaction, and an internal alkyne can be reacted with an azide according to the ruthenium-catalyzed azide-alkyne coupling reaction, to provide a staged bis-triazole synthesis. The order of reaction of the alkynes and azides can be controlled in some cases by the specific reaction conditions utilized. FIG. 13 provides a schematic example of such a staged synthesis, while FIG. 14 provides a specific example. In FIG. 13 compound (top) having a terminal ethyn substituent and a 1-iodoethyne substituent is sequentially reacted via a CuAAC reaction and then the copper catalyzed coupling of the present invention (left branch), or via copper catalyzed coupling of the present invention and then a CuAAC reaction, (right branch) to afford a bis-triazole compound (bottom).

In FIG. 14, bis-alkyne 70 is sequentially reacted as in FIG. 13 to form intermediates 71 or 72 and ultimately provide bis-triazole 73, which includes two differently substituted triazole moieties.

Figure 15:
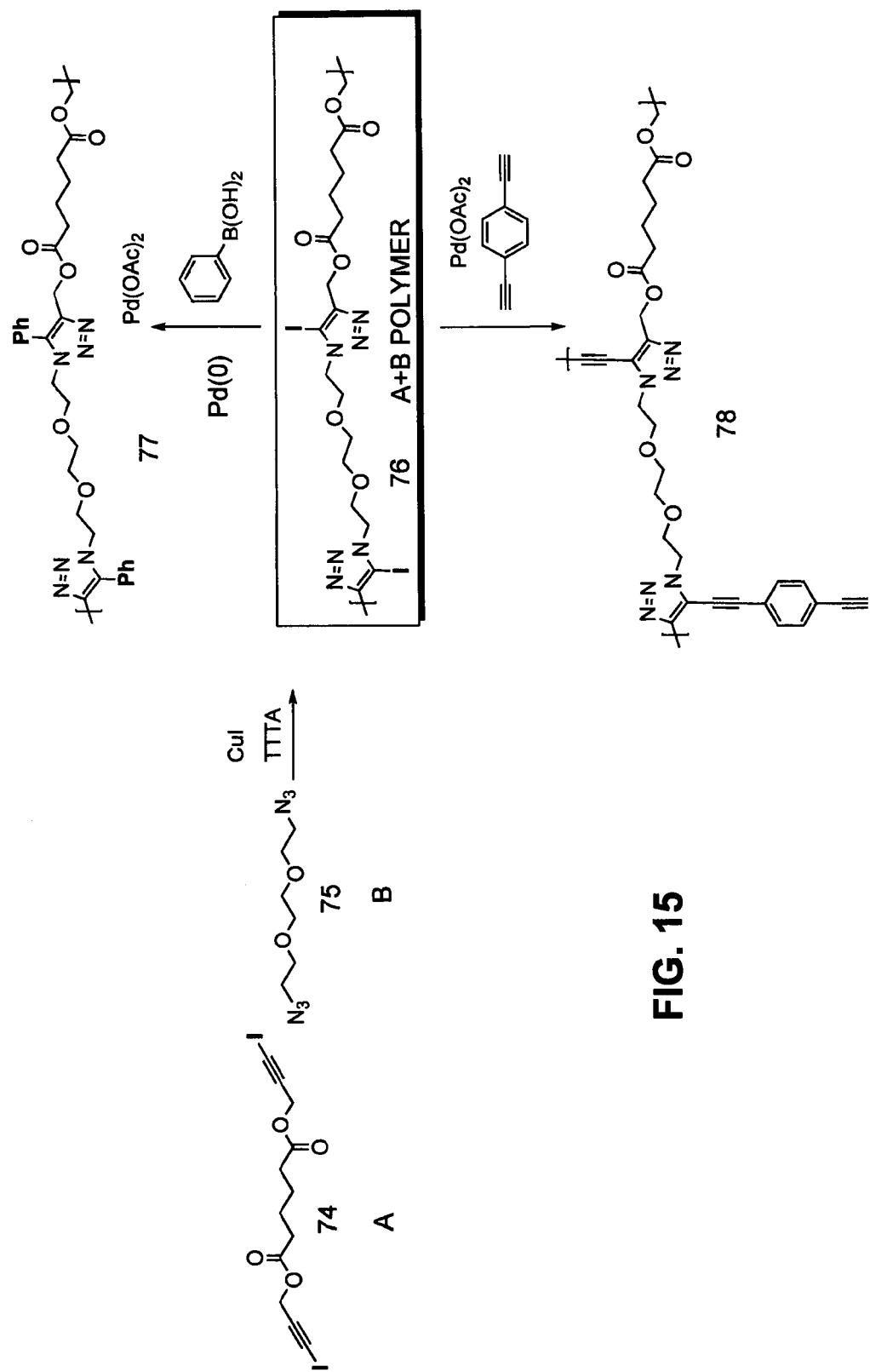
FIG. 15 provides an example of a polymer synthesis utilizing a bis-1-iodoalkyne (A) with a bis-azide (B) to afford an A+B type polytriazole.

FIG. 15 provides an additional example of a polymer synthesis utilizing a bis-1-iodoalkyne (74, A) with a bis-azide (75, B) to afford an A+B type polytriazole 76.

Polytriazole 76 can be further funtionalized by Pd(0) coupling with phenylboronic acid to form phenyltriazole derivative 77, or by Pd acetate mediated coupling with 1,4-bis-ethynylbenzene to form polyethynylated derivative 78.

Additional details of the present methods are illustrated below with reference to detailed synthetic procedures and characterization of reagents, starting materials, and or products of use in or prepared by the methods of the present invention.

General Methods. $^1$H and $^{13}$C NMR spectra were recorded on Bruker DRX-500, Bruker AMX-400 instruments and the chemical shifts (δ) are expressed in parts per million relative to residual $CHCl_3$, acetone, or DMSO as internal standards. Proton magnetic resonance ($^1$H NMR) spectra were recorded at 600, or 500 MHz. Carbon magnetic resonance ($^{13}$C NMR) spectra were recorded at 150, or 125 MHz. NMR acquisitions were performed at 295 K unless otherwise noted. Abbreviations are: s, singlet; d, doublet; t, triplet; q, quartet, p, pentet; br s, broad singlet. Infrared spectra were recorded as pure undiluted samples using ThermoNicolet Avatar 370 Fourier transform infrared spectrometer with a Smart MIRacle™ HATR attachment. Melting points (mp) were determined using a Barnstead Electrothermal digital melting point apparatus (Model IA9300) and are uncorrected. GCMS data were recorded on an Agilent 7890A GC system with an Agilent 5975C Inert MSD system operating in the electron impact (EI+) mode. HPLC was performed on an Agilent 1100LC/MSD with an Agilent 1100 SL mass spectrometer (electrospray ionization, ES) eluting with 0.1% trifluoroacetic acid in $H_2O$ and 0.05% trifluoroacetic acid in $CH_3CN$. High resolution mass spectrometry was performed on an Agilent ES-TOF instrument. All chromatography was performed using Merck silica gel (40-63 μM) with the indicated solvent mixtures. All starting materials were purchased from Aldrich, Acros, Fisher, Lancaster, or TCI chemical companies and used as received. Solvents were purchased from Fisher or Acros chemical companies and used as received (no extra drying, distillation or special handling practices were employed).

Synthesis of N-iodomorpholine-hydrogen iodide: Procedure adapted from Koyama, M.; Ohtani, N.; Kai, F.; Moriguchi, I.; Inouye, S. *J. Med. Chem.* 1987, 30, 552-562. A solution of iodine (25.40 g, 0.10 mol) in MeOH (400 ml) was treated dropwise with morpholine (8.71 ml, 0.10 mol). On addition the solution rapidly changed from dark purple-brown to light orange and a fine orange precipitate was generated. The solution was stirred for about 45 min then solid was isolated by filtration. The solid was transferred to a round bottom flask and dried under vacuum. Once the material reached a free flowing consistency it was placed in a plastic bottle and stored in a refrigerator. This procedure gave N-iodomorpholine-hydrogen iodide as an orange crystalline powder (30.34 g, 0.09 mol, 89%) which was used without further purification or characterization.

General procedure for the synthesis of 1-iodoalkynes-1-iodo-phenylacetylene (1): Phenylacetylene (8.17 g, 80.00 mmol) was dissolved in THF (200 mL) and treated with CuI (0.76 g, 4.00 mmol) and N-iodomorpholine (30.00 g, 88.00 mmol). The reaction mixture was stirred at room temperature for 45 minutes, after which a fine white precipitate had formed. The suspension was poured onto a pad of neutral alumina (400 mL) and the filtrate was collected under vacuum. The solid phase was washed with DCM (4×100 mL) and the combined organic fractions were pooled and concentrated by evaporation, giving 1 (16.61 g, 72.82 mmol, 91%) as a yellow oil. This material was used without further purification.

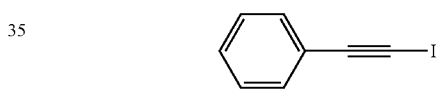

1-Iodo-phenylacetylene (1). yellow oil; IR (υ[cm$^{-1}$]) 3054, 2171, 1596, 1487, 1442, 1069, 1025, 915, 751, 687; $^1$H NMR (500 MHz, $CDCl_3$) δ=7.45-7.40 (m, J=9.1, 3.9, 2H), 7.33-7.27 (m, 3H); $^{13}$C NMR (126 MHz, $CDCl_3$) δ=132.5, 129.0, 128.4, 123.6, 94.4, 6.4.

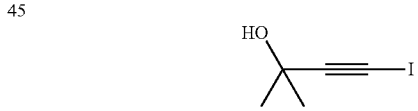

4-Iodo-2-methylbut-3-yn-2-ol (24). Synthesized from 2-methylbut-3-yn-2-ol using general procedure, 4.3 g, 20.5 mmol, 87%; clear oil; IR (υ[cm$^{-1}$]) 3359, 2981, 2933, 2179, 1697, 1363, 1219, 1161, 956, 903, 770; $^1$H NMR (600 MHz, $CDCl_3$) δ=1.50 (s, 6H); $^{13}$C NMR (151 MHz, $CDCl_3$) δ=99.3, 67.0, 31.5, -0.4; HRMS (ESI-TOF) (m/z): [M+Na]$^+$ calcd for $C_5H_7INaO$, 232.9434; found 232.9443.

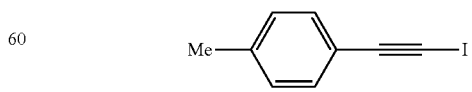

1-(Iodoethynyl)-4-methylbenzene (25). Synthesized from 1-ethynyl-4-methylbenzene using general procedure, 19.7 g, 81.0 mmol, 89%; low melting solid; IR (υ[cm$^{-1}$]) 3027, 2164, 1904, 1505, 1446, 1178, 1116, 1019, 706; $^1$H NMR (600

MHz, CDCl$_3$) δ=7.32 (d, J=8.1, 2H), 7.11 (d, J=8.0, 2H), 2.34 (s, 3H); $^{13}$C NMR (151 MHz, CDCl$_3$) δ=139.2, 132.4, 129.2, 120.5, 94.4, 21.7, 5.2.

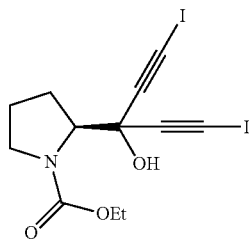 [SMILES: CCOC(=O)N1CCC[C@H]1C(O)(C#CI)C#CI]

(S)-Ethyl 2-(3-hydroxy-1,5-diiodopenta-1,4-diyn-3-yl)pyrrolidine-1-carboxylate (26). Synthesized from (S)-ethyl 2-(3-hydroxypenta-1,4-diyn-3-yl)pyrrolidine-1-carboxylate using general procedure, 1.8 g, 3.8 mmol, 84%; white powder; mp=124-129° C. (dec.); IR (υ[cm$^{-1}$]) 2975, 2884, 2182, 1643, 1422, 1382, 1348, 1202, 1127, 1028, 786; $^1$H NMR (600 MHz, CDCl$_3$) δ=7.28 (s, 1H), 4.24-4.12 (m, 3H), 3.65 (br s, 1H), 3.42-3.32 (m, 1H), 2.24 (dt, J=14.5, 7.1, 1H), 2.20-2.09 (m, 1H), 2.09-2.00 (m, 1H), 1.80-1.69 (m, 1H), 1.28 (t, J=7.1, 3H); $^{13}$C NMR (151 MHz, CDCl$_3$) δ=159.2, 93.0, 92.5, 72.0, 68.1, 62.9, 48.7, 30.1, 24.0, 14.8, 3.6, 2.8; HRMS (ESI-TOF) (m/z): [M+Na]$^+$ calcd for C$_{12}$H$_{13}$I$_2$NNaO$_3$, 495.8877; found 495.8870.

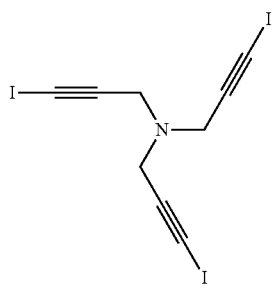 [SMILES: IC#CCN(CC#CI)CC#CI]

Tris(3-iodoprop-2-ynyl)amine (27). Synthesized from tripropargylamine using general procedure, 12.9 g, 24.0 mmol, 79%; white powder; WARNING: sample detonates when heated above 170° C., use caution when handling this compound; IR (υ[cm$^{-1}$]) 2823, 2194, 1434, 1340, 1326, 1121, 1092, 1000, 970, 943; $^1$H NMR (600 MHz, DMSO) δ=3.46 (s, 6H); $^{13}$C NMR (151 MHz, DMSO) δ=88.1, 43.2, 10.1; HRMS (ESI-TOF) (m/z): [M+H]$^+$ calcd for C$_9$H$_7$I$_3$N, 509.7707; found 509.7708.

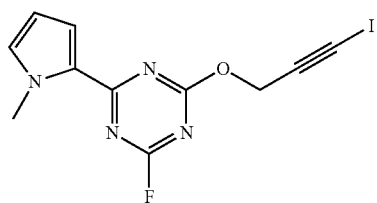 [SMILES: Cn1cccc1-c1nc(F)nc(OCC#CI)n1]

2-Fluoro-4-(3-iodoprop-2-ynyloxy)-6-(1-methyl-1H-pyrrol-2-yl)-1,3,5-triazine. 2,4-difluoro-6-(1-methyl-1H-pyrrol-2-yl)-1,3,5-triazine (0.75 g, 3.82 mmol) was dissolved in acetonitrile (10 ml) and treated sequentially with 3-iodoprop-2-yn-1-ol$^3$ (0.626 g, 3.44 mmol) and DIPEA (0.666 ml, 3.82 mmol). The sample was stirred at r.t. for 25 min, after which a precipitate formed and was isolated by filtration. The solid was washed with hexanes and dried under vacuum to give 26 as a white solid, 1.31 g, 3.66 mmol, 96%; mp=155-158° C.; IR (υ[cm$^{-1}$]) 3119, 2983, 2191, 1593, 1525, 1433, 1096, 986, 857, 755; $^1$H NMR (600 MHz, CDCl$_3$) δ=7.45 (dd, J=3.9, 1.5, 1H), 6.91 (s, 1H), 6.22 (dd, J=3.8, 2.5, 1H), 5.18 (s, 2H), 4.09 (s, 3H); $^{13}$C NMR (151 MHz, CDCl$_3$) δ=171.3 (dd, J=328.6, 15.5), 171.3, 169.8, 133.1, 127.9, 121.6, 109.9, 87.6, 57.5, 38.9, 6.1; HRMS (ESI-TOF) (m/z): [M+H]$^+$ calcd for C$_{11}$H$_9$FIN$_4$, 358.9800; found 358.9796.

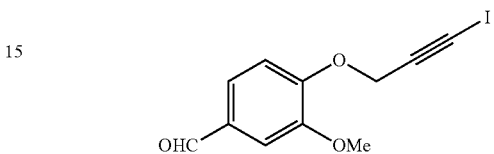

4-(3-Iodoprop-2-ynyloxy)-3-methoxybenzaldehyde. Synthesized from 3-methoxy-4-(prop-2-ynyloxy)benzaldehyde using general procedure, 1.43 g, 4.52 mmol, 86%; yellow solid; mp=121-127° C.; IR (υ[cm$^{-1}$]) 3003, 2849, 2206, 1686, 1584, 1506, 1280, 1157, 1027, 982, 803, 733, 663; $^1$H NMR (600 MHz, CDCl$_3$) δ=9.85 (s, 1H), 7.44 (dd, J=8.2, 1.5, 1H), 7.40 (s, 1H), 7.09 (d, J=8.2, 1H), 4.96 (s, 2H), 3.92 (d, J=14.3, 3H); $^{13}$C NMR (151 MHz, CDCl$_3$) δ=191.1, 152.3, 150.1, 131.1, 126.6, 112.6, 109.6, 88.1, 58.2, 56.2, 6.8; HRMS (ESI-TOF) (m/z): [M+H]$^+$ calcd for C$_{11}$H$_{10}$IO$_3$, 316.9669; found 316.9677.

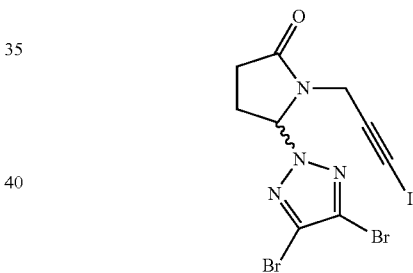

5-(4,5-Dibromo-2H-1,2,3-triazol-2-yl)-1-(3-iodoprop-2-ynyl)pyrrolidin-2-one. Synthesized from 5-(4,5-dibromo-2H-1,2,3-triazol-2-yl)-1-(prop-2-ynyl)pyrrolidin-2-one$^5$ using general procedure, 1.21 g, 2.55 mmol, 89%; waxy solid; IR (υ[cm$^{-1}$]) 2980, 2191, 1729, 1375, 1241, 1048, 824, 685; $^1$H NMR (600 MHz, CDCl$_3$) δ=6.10 (d, J=7.6, 1H), 4.36 (d, J=17.8, 1H), 3.91 (d, J=17.8, 1H), 2.92-2.84 (m, 1H), 2.65-2.58 (m, 1H), 2.54-2.39 (m, 2H); $^{13}$C NMR (151 MHz, CDCl$_3$) δ=174.29, 126.4, 86.7, 73.1, 32.4, 28.6, 25.5, 1.0.; HRMS (ESI-TOF) (m/z): [M+H]$^+$ calcd for C$_9$H$_8$Br$_2$IN$_4$O, 472.8104; found 472.8095.

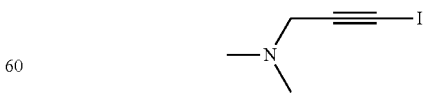

3-Iodo-N,N-dimethylpropargylamine. Synthesized from N,N-dimethylpropargylamine using general procedure, 3.77 g, 18.04 mmol, 75%; white solid; mp=135° C. (dec.); IR (υ[cm$^{-1}$]) 2975, 2944, 2876, 2787, 2162, 1471, 1326, 1040, 958, 809; $^1$H NMR (600 MHz, CDCl$_3$) δ=3.40 (s, 2H), 2.27

(s, 6H); $^{13}$C NMR (151 MHz, CDCl$_3$) δ=89.0, 49.9, 44.3, 0.01; HRMS (ESI-TOF) (m/z): [M+H]$^+$ calcd for C$_5$H$_9$IN, 209.9774; found 209.9781.

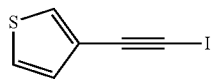

3-(Iodoethynyl)thiophene. Synthesized from 3-ethylylthiophene using general procedure, 0.985 g, 4.21 mmol, 91%; brown oil; IR (υ[cm$^{-1}$]) 3100, 2174, 1570, 1355, 1222, 1160, 1078, 945, 767, 688; $^1$H NMR (500 MHz, CDCl$_3$) δ=7.56-7.55 (m, 1H), 7.34 (dd, J=5.0, 2.9, 1H), 7.21-7.18 (m, 1H); $^{13}$C NMR (151 MHz, CDCl$_3$) δ=130.5, 130.2, 125.4, 122.7, 89.4, 6.2.

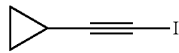

(Iodoethynyl)cyclopropane. Synthesized from ethynylcyclopropane using general procedure, 2.39 g, 12.45 mmol, 82%; yellow oil; IR (υ[cm$^{-1}$]) 3091, 3009, 2974, 2186, 1681, 1615, 1448, 1377, 1220, 1053, 1026, 962, 773; $^1$H NMR (600 MHz, CDCl$_3$) δ=1.39-1.31 (m, 1H), 0.79-0.68 (m, 4H).; $^{13}$C NMR (151 MHz, CDCl$_3$) δ=97.4, 8.4, 1.8, −11.5.

General procedure for the synthesis of 5-iodotriazoles using CuI-TEA-5-iodo-4-phenyl-1-(3-(trifluoromethyl)benzyl)-1H-1,2,3-triazole (3): Compounds 1 (0.23 g, 1.00 mmol) and 2 (0.20 g, 1.00 mmol) were dissolved in THF (5 mL). The solution was treated sequentially with CuI (9.52 mg, 0.05 mmol) and TEA (0.28 ml, 2.00 mmol) and then allowed to stir at room temperature for 6 hours. After this time the reaction was quenched by adding 1 mL of 10% NH$_4$OH solution. The volatile components were removed by evaporation, and the resulting residue was suspended in water and diethyl ether. A precipitate formed upon vigorous stirring and was isolated by filtration, giving 3 (0.39 g, 0.90 mmol, 90%) as a fine white powder.

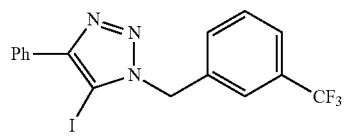 [SMILES: FC(F)(F)c1cccc(Cn2nnc(-c3ccccc3)c2I)c1]

5-Iodo-4-phenyl-1-(3-(trifluoromethyl)benzyl)-1H-1,2,3-triazole (3). mp=193-195° C. (dec.); IR (υ[cm$^{-1}$]) 3132, 1329, 1165, 1118, 1076, 767, 697; $^1$H NMR (600 MHz, CDCl$_3$) δ=7.96-7.90 (m, 2H), 7.62 (s, 1H), 7.59 (d, J=7.5, 1H), 7.51-7.42 (m, 4H), 7.41-7.37 (m, 1H), 5.71 (s, 2H); $^{13}$C NMR (151 MHz, CDCl$_3$) δ=150.6, 135.5, 131.6 (q, J=32.7), 131.4, 130.2, 129.8, 129.0, 128.8, 127.6, 125.7 (q, J=3.7), 125.0 (q, J=3.8), 123.9 (q, J=272.4), 76.6, 54.0; HRMS (ESI-TOF) (m/z): [M+H]$^+$ calcd for C$_{16}$H$_{12}$F$_3$IN$_3$, 430.0023; found 430.0026.

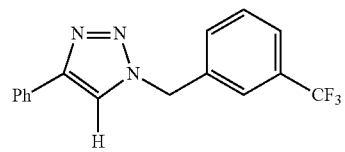

4-Phenyl-1-(3-(trifluoromethyl)benzyl)-1H-1,2,3-triazole (4). Isolated as a by-product from initial catalyst screening; mp=126-127° C.; IR (υ[cm$^{-1}$]) 3073, 1323, 1153, 1075, 773, 699; $^1$H NMR (600 MHz, CDCl$_3$) δ=7.81-7.76 (m, 2H), 7.70 (s, 1H), 7.61 (d, J=7.7, 1H), 7.57 (s, 1H), 7.50 (t, J=7.7, 1H), 7.46 (d, J=7.8, 1H), 7.39 (t, J=7.6, 2H), 7.34-7.29 (m, 1H), 5.62 (s, 2H); $^{13}$C NMR (151 MHz, CDCl$_3$) δ=148.8, 135.9, 131.8 (q, J=32.5), 131.5, 130.4, 130.0, 129.1, 128.6, 126.0, 125.9 (q, J=3.8), 124.9 (q, J=3.7), 123.9 (q, J=272.8), 119.7, 53.8; HRMS (ESI-TOF) (m/z): [M+H]$^+$ calcd for C$_{16}$H$_{13}$F$_3$N$_3$, 304.1056; found 304.1059.

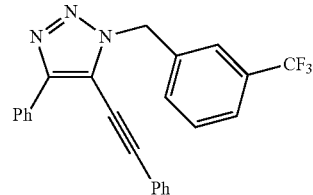 [SMILES: FC(F)(F)c1cccc(Cn2nnc(-c3ccccc3)c2C#Cc2ccccc2)c1]

4-Phenyl-5-(phenylethynyl)-1-(3-(trifluoromethyl)benzyl)-1H-1,2,3-triazole (5). Isolated as a by-product from initial catalyst screening; mp=115-118° C.; IR (υ[cm$^{-1}$]) 2963, 2219, 1504, 1453, 1328, 1161, 1071, 773, 690; $^1$H NMR (600 MHz, CDCl$_3$) δ=8.17 (d, J=7.4, 2H), 7.71 (s, 1H), 7.59 (d, J=7.7, 1H), 7.55 (d, J=7.7, 1H), 7.51-7.34 (m, 9H), 5.71 (s, 2H); $^{13}$C NMR (151 MHz, CDCl$_3$) δ=148.5, 135.8, 131.8, 131.7, 131.5 (q, J=32.5), 130.3, 130.1, 129.8, 129.0, 128.9, 128.7 (q, J=165.0), 126.4, 125.7 (q, J=3.6), 125.2 (q, J=3.7), 124.9, 123.1, 121.3, 117.4, 103.0, 75.4, 52.6, 1.2; HRMS (ESI-TOF) (m/z): [M+H]$^+$ calcd for C$_{24}$H$_{17}$F$_3$N$_3$, 404.1369; found 404.1372.

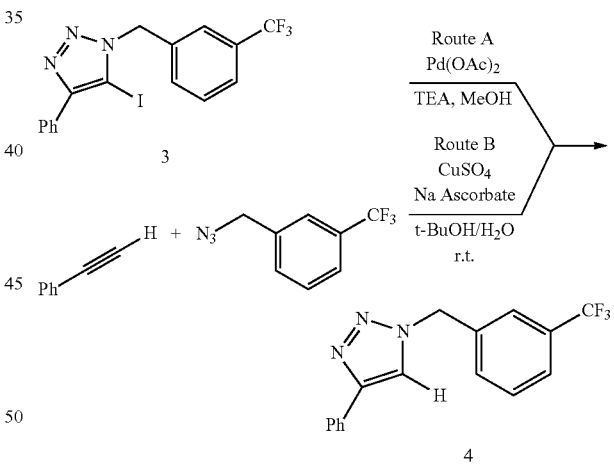

Assignment of regiochemistry for 5-iodo-4-phenyl-1-(3-(trifluoromethyl)benzyl)-1H-1,2,3-triazole (3): Iodotriazole 3 was reduced to give the corresponding 5-proto-triazole 4 (Route A). Concurrently, an authentic sample of 5-proto-triazole 4 was synthesized using the established CuAAC protocol (Route B). The physical and spectroscopic characteristics of the samples obtained via both routes were compared and found to be identical.

Route A: Pd(OAc)$_2$ (0.449 g, 2.000 mmol) was added to a solution of 3 (0.858 g, 2 mmol) and TEA (0.281 ml, 2.000 mmol) in MeOH (10 ml). The sample was warmed to 55° C. for 4 h and monitored by LC-MS. Once the starting material had been consumed the sample was cooled and the volatile components were removed under vacuum. The crude residue was then purified by column chromatography (9:1 Hex: EtOAc-4:1 Hex:EtOAc) to give 4 (0.59 g, 1.945 mmol, 97% yield) as a white solid.

Route B: Phenylacetylene (0.409 g, 4 mmol) and 3-(trifluoromethyl)benzyl azide (0.805 g, 4.00 mmol) were dissolved in 4:1 t-BuOH/H$_2$O (25 ml) and then treated sequentially with a 1M aq. solution of CuSO$_4$ (0.200 ml, 0.200 mmol) followed by solid sodium ascorbate (0.079 g, 0.400 mmol). The sample was stirred at r.t. for 4 h. during which time a precipitate formed. The sample was quenched with 10 mL of 10% NH$_4$OH aq. and the solid was isolated by filtration. The solid was washed with water and dried under vacuum, giving 4 (1.112 g, 3.67 mmol, 92% yield) as a white solid.

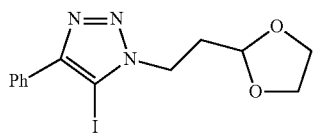 [SMILES: Ic1c(-c2ccccc2)nnn1CCC1OCCO1]

1-(2-(1,3-Dioxolan-2-yl)ethyl)-5-iodo-4-phenyl-1H-1,2,3-triazole (6). Synthesized from 1-iodo-phenylacetylene and 2-(2-azidoethyl)-1,3-dioxolane using general procedure, 3.64 g, 9.80 mmol, 98%; white powder; mp=118-121° C. (dec.); IR (υ[cm$^{-1}$]) 3052, 2885, 1446, 1400, 1222, 1133, 1048, 900, 769, 714; $^1$H NMR (600 MHz, CDCl$_3$) δ=7.94-7.88 (m, 2H), 7.44 (t, J=7.6, 2H), 7.38 (t, J=7.4, 1H), 5.01 (t, J=4.2, 1H), 4.61-4.55 (m, 2H), 4.05-3.96 (m, 2H), 3.93-3.84 (m, 2H), 2.40-2.31 (m, 2H); $^{13}$C NMR (151 MHz, CDCl$_3$) δ=150.0, 130.5, 128.8, 128.7, 127.7, 101.7, 76.6, 65.4, 46.3, 33.8; HRMS (ESI-TOF) (m/z): [M+H]$^+$ calcd for C$_{13}$H$_{15}$IN$_3$O$_2$, 372.0203; found 372.0203.

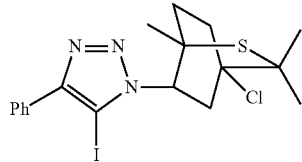 [SMILES: CC12CCC(Cl)(CC1n1nnc(-c3ccccc3)c1I)C(C)(C)S2]

1-(4-chloro-1,3,3-trimethyl-2-thiabicyclo[2.2.2]octan-7-yl)-5-iodo-4-phenyl-1H-1,2,3-triazole (7). Synthesized from 1-iodo-phenylacetylene and 7-azido-4-chloro-1,3,3-trimethyl-2-thiabicyclo[2.2.2]octane using general procedure, 0.153 g, 0.323 mmol, 73%; mp=157-159° C. (dec.); IR (υ[cm$^{-1}$]) 2979, 2103, 1447, 1387, 1326, 1240, 1160, 985, 772, 712; $^1$H NMR (CDCl$_3$, 600 MHz,) δ 7.94-7.92 (m, 2H), 7.48-7.46 (m, 2H), 7.42-7.39 (m, 1H), 5.25 (ddd, J=11.2, 4.8, 2.1, 1H), 3.11 (ddd, J=11.7, 11.2, 3.2, 1H), 2.73 (dd, J=12.7, 5.3, 1H), 2.75-2.60 (m, 1H), 2.45-2.39 (m, 1H), 1.93-1.88 (m, 1H), 1.82 (s, 3H), 1.77 (s, 3H), 1.52 (s, 3H); $^{13}$C NMR (151 MHz, CDCl$_3$) δ=149.6, 130.4, 128.9, 128.8, 127.9, 79.4, 76.9, 72.4, 72.4, 68.8, 65.7, 42.5, 37.1, 36.4, 30.9, 30.5, 19.8; HRMS (ESI-TOF) (m/z): [M+H]$^+$ calcd for C$_{18}$H$_{22}$ClIN$_3$S, 474.0262; found 474.0266.

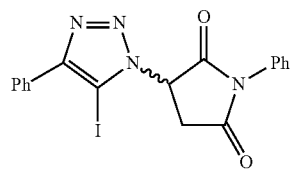 [SMILES: O=C1CC(n2nnc(-c3ccccc3)c2I)C(=O)N1c1ccccc1]

3-(5-iodo-4-phenyl-1H-1,2,3-triazol-1-yl)-1-phenylpyrrolidine-2,5-dione (8). Synthesized from 1-iodo-phenylacetylene and 3-azido-1-phenylpyrrolidine-2,5-dione using general procedure, 0.443 g, 0.997 mmol, 76%; mp=164-169° C. (dec.); IR (υ[cm$^{-1}$]) 2933, 1792, 1719, 1497, 1379, 1149, 786, 694; $^1$H NMR (CDCl$_3$, 600 MHz,) δ 7.93-7.92 (m, 2H), 7.52-7.47 (m, 4H), 7.45-7.42 (m, 2H), 7.39-7.37 (m, 2H), 5.91 (dd, J=9.4, 5.8, 1H), 3.71 (dd, J=18.3, 5.8, 1H), 3.58 (dd, J=18.3, 9.8, 1H); $^{13}$C NMR (CDCl$_3$, 150 MHz) δ 172.4, 170.8, 151.6, 131.9, 130.4, 130.25, 130.1, 129.9, 129.5, 128.5, 127.2, 78.7, 58.4, 36.3; HRMS (ESI-TOF) (m/z): [M+H]$^+$ calcd for C$_{18}$H$_{14}$IN$_4$O$_2$, 445.0156; found 445.0159.

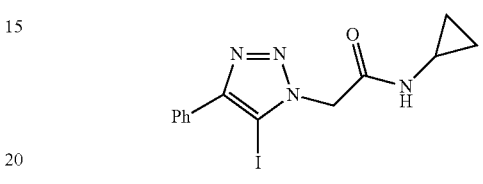

N-cyclopropyl-2-(5-iodo-4-phenyl-1H-1,2,3-triazol-1-yl) acetamide (9). Synthesized from 1-iodo-phenylacetylene and 2-azido-N-cyclopropylacetamide using general procedure; 0.364 g, 0.989 mmol, 90%; mp=197-198° C. (dec.); IR (υ[cm$^{-1}$]) 3287, 3071, 2971, 1661, 1557, 1407, 1269, 1129, 985, 952, 769, 686; $^1$H NMR (DMSO-d$_6$, 600 MHz,) δ 8.53 (d, J=3.6, 1H), 7.88-7.87 (m, 2H), 7.50-7.48 (m, 2H), 7.41-7.39 (m, 1H), 5.09 (s, 2H), 2.68-2.63 (m, 1H), 0.64 (dt, J=7.0, 5.0, 2H), 0.45 (dt, J=6.9, 4.3, 2H); $^{13}$C NMR (DMSO-d$_6$, 150 MHz) δ 167.1, 149.7, 131.9, 130.0, 129.6, 128.1, 84.1, 53.8, 23.7, 6.9; HRMS (ESI-TOF) (m/z): [M+H]$^+$ calcd for C$_{13}$H$_{14}$IN$_4$O, 369.0207; found 369.0209.

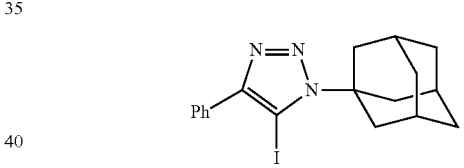

1-Adamantyl-5-iodo-4-phenyl-1H-1,2,3-triazole (10). Synthesized from 1-iodo-phenylacetylene and 1-azido-adamantane using general procedure; 0.278 g, 0.686 mmol, 46%, mp=224-225° C. (dec.); IR (υ[cm$^{-1}$]) 2912, 2849, 1466, 1444, 1317, 1247, 1153, 1018, 983, 767, 692; $^1$H NMR (600 MHz, CDCl$_3$) δ=7.78-7.74 (m, 2H), 7.43 (t, J=7.5, 2H), 7.38 (t, J=7.4, 1H), 2.59 (d, J=2.5, 6H), 2.29 (s, 3H), 1.83-1.74 (m, 6H); $^{13}$C NMR (151 MHz, CDCl$_3$) δ=152.0, 130.9, 129.0, 128.6, 128.5, 69.8, 64.4, 41.6, 36.0, 30.0; HRMS (ESI-TOF) (m/z): [M+H]$^+$ calcd for C$_{18}$H$_{21}$IN$_3$, 406.0775; found 406.0771.

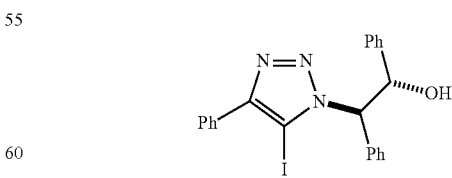

trans-2-(5-iodo-4-phenyl-1H-1,2,3-triazol-1-yl)-1,2-diphenylethanol (11). Synthesized from 1-iodo-phenylacetylene and trans-2-azido-1,2-diphenylethanol using general procedure; 0.196 g, 0.419 mmol, 96%; mp=152-154° C. (dec.); IR (υ[cm$^{-1}$]) 3296, 2971, 1493, 1380, 1325, 1159, 1105, 950, 770, 744; $^1$H NMR (600 MHz, CDCl$_3$) δ=7.83-7.79 (m, 2H), 7.41 (t, J=7.6, 2H), 7.37-7.34 (m, 1H), 7.33-7.22 (m, 10H), 5.86 (dd, J=5.6, 2.4, 1H), 5.66 (d, J=5.7, 1H), 3.75 (br s, 1H, OH); $^{13}$C NMR (151 MHz, CDCl$_3$) δ=149.4, 139.3, 134.1, 130.1, 129.2, 129.0, 128.9, 128.7, 128.6, 128.5, 128.5, 127.7, 126.9, 78.5, 75.6, 71.4; HRMS (ESI-TOF) (m/z): [M+H]$^+$ calcd for C$_{22}$H$_{19}$IN$_3$O, 468.0567; found 468.0571.

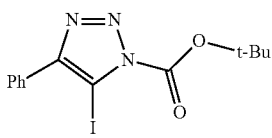 [SMILES: CC(C)(C)OC(=O)n1nnc(-c2ccccc2)c1I]

tert-butyl 5-iodo-4-phenyl-1H-1,2,3-triazole-1-carboxylate (12). Synthesized from 1-iodo-phenylacetylene and tert-butyl carbamoylazide using general procedure, sample purified by column chromatography (4:1 Hex:EtOAc); 0.208 g, 0.560 mmol, 77%; mp=87-90° C.; IR (υ[cm$^{-1}$]) 2984, 1774, 1468, 1394, 1342, 1287, 1142, 959, 847, 752, 693; $^1$H NMR (600 MHz, CDCl$_3$) δ=7.95-7.91 (m, 2H), 7.48-7.43 (m, 3H), 1.69 (s, 9H); $^{13}$C NMR (150 MHz, CDCl$_3$) δ=153.0, 145.0, 130.1, 128.8, 128.5, 128.5, 96.3, 88.0, 28; HRMS (ESI-TOF) (m/z): [M+Na]$^+$ calcd for C$_{13}$H$_{14}$IN$_3$NaO$_2$, 394.0023; found 394.0024.

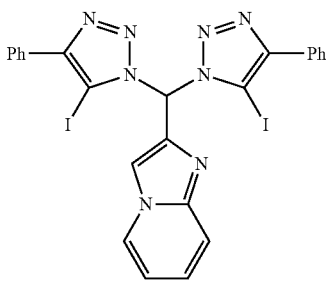 [SMILES: Ic1c(-c2ccccc2)nnn1C(c1cn2ccccc2n1)n1nnc(-c2ccccc2)c1I]

2-(bis(5-iodo-4-phenyl-1H-1,2,3-triazol-1-yl)methyl)imidazo[1,2-c]pyridine (13). Synthesized from 1-iodo-phenylacetylene and 2-(diazidomethyl)imidazo[1,2-a]pyridine using general procedure; 0.618 g, 0.922 mmol, 84%; mp=183-185° C. (dec.); IR (υ[cm$^{-1}$]) 3080, 1500, 1474, 1444, 1330, 1128, 982, 809, 754, 739, 693; $^1$H NMR (DMSO-d$_6$, 600 MHz,) δ 8.60-8.59 (m, 1H), 8.46 (br s, 1H), 8.00 (br s, 1H), 7.92-7.90 (m, 4H), 7.60 (br s, 1H), 7.53-7.50 (m, 4H), 7.45-7.43 (m, 2H), 7.35-7.32 (m, 1H), 6.99-6.96 (m, 1H); $^{13}$C NMR (DMSO-d$_6$, 150 MHz) δ 150.4, 131.2, 130.1, 130.05, 128.9, 128.4, 127.4, 118.4, 114.3, 84.0, 73.4; HRMS (ESI-TOF) (m/z): [M+H]$^+$ calcd for C$_{24}$H$_{17}$I$_2$N$_8$, 670.9660; found 670.9657.

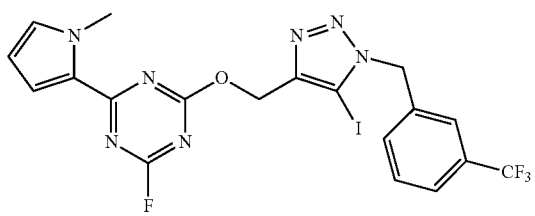 [SMILES: Cn1cccc1-c1nc(F)nc(OCc2nnn(Cc3cccc(C(F)(F)F)c3)c2I)n1]

2-Fluoro-4-((5-iodo-1-(3-(trifluoromethyl)benzyl)-1H-1,2,3-triazol-4-yl)methoxy)-6-(1-methyl-1H-pyrrol-2-yl)-1,3,5-triazine (14). Synthesized from 2-fluoro-4-(3-iodoprop-2-ynyloxy)-6-(1-methyl-1H-pyrrol-2-yl)-1,3,5-triazine and 3-trifluoromethyl-benzylazide using general procedure; 0.311 g, 0.556 mmol, 80%; mp=185-187° C. (dec.); IR (υ[cm$^{-1}$]) 3130, 3059, 1595, 1555, 1418, 1357, 1173, 1104, 1056, 911, 803, 756; $^1$H NMR (600 MHz, CDCl$_3$) δ=7.61-7.58 (m, 2H), 7.50-7.41 (m, 3H), 6.90 (s, 1H), 6.21 (dd, J=3.9, 2.5, 1H), 5.64 (s, 2H), 5.56 (s, 2H), 4.09 (s, 3H); $^{13}$C NMR (151 MHz, CDCl$_3$) δ=171.5 (dd, J=361.1, 15.4), 171.3, 169.8, 135.0, 133.0, 131.6 (q, J=32.8), 131.5, 129.9, 125.9 (q, J=3.6), 125.1 (q, J=3.7), 123.9 (q, J=272.4), 121.5, 81.6, 61.7, 54.0, 39.0; HRMS (ESI-TOF) (m/z): [M+H]$^+$ calcd for C$_{18}$H$_{15}$F$_4$IN$_7$O, 560.0313; found 560.0311.

2-(5-Iodo-1-(3-(trifluoromethyl)benzyl)-1H-1,2,3-triazol-4-yl)propan-2-ol (15). Synthesized from 4-iodo-2-methylbut-3-yn-2-ol and 3-trifluoromethyl-benzylazide using general procedure; 3.82 g, 9.30 mmol, 93%; mp=77-80° C.; IR (υ[cm$^{-1}$]) 3385, 2981, 2938, 1326, 1170, 1120, 1074, 763, 699; $^1$H NMR (600 MHz, CDCl$_3$) δ=7.58-7.57 (m, 2H), 7.48-7.45 (m, 1H), 7.42-7.41 (m, 1H), 5.62 (s, 2H), 1.66 (s, 6H); $^{13}$C NMR (151 MHz, CDCl$_3$) δ=156.4, 135.4, 131.5 (q, J=33.2), 131.4, 129.8, 125.7 (q, J=3.7), 125.1 (q, J=3.8), 123.9 (q, J=272.4), 74.2, 69.7, 53.8, 30.1; HRMS (ESI-TOF) (m/z): [M+H]$^+$ calcd for C$_{13}$H$_{14}$F$_3$IN$_3$O, 412.0128; found 412.0126.

5-Iodo-4-(thiophen-3-yl)-1-(3-(trifluoromethyl)benzyl)-1H-1,2,3-triazole (16). Synthesized from 3-(iodoethynyl)thiophene and 3-trifluoromethyl-benzylazide using general procedure; 0.994 g, 2.284 mmol, 99%; mp=153-158° C. (dec.); IR (υ[cm$^{-1}$]) 3121, 1326, 1194, 1163, 1096, 1075, 853, 792, 702; $^1$H NMR (600 MHz, CDCl$_3$) δ=7.97-7.93 (m, 1H), 7.75 (d, J=5.0, 1H), 7.59 (d, J=7.7, 2H), 7.58 (s, 1H), 7.47 (t, J=7.7, 1H), 7.45-7.38 (m, 2H), 5.69 (s, 2H); $^{13}$C NMR (151 MHz, CDCl$_3$) δ=147.5, 135.4, 131.6 (q, J=32.7), 131.3, 131.0, 129.8, 126.7, 126.2, 125.7 (q, J=3.7), 124.9 (q, J=3.8), 123.9 (q, J=272.4), 123.5, 76.0, 53.9; HRMS (ESI-TOF) (m/z): [M+H]$^+$ calcd for C$_{14}$H$_{10}$F$_3$IN$_3$S, 435.9587; found 435.9586.

4-((5-Iodo-1-(3-(trifluoromethyl)benzyl)-1H-1,2,3-triazol-4-yl)methoxy)-3-methoxybenzaldehyde (17). Synthesized from 4-(3-iodoprop-2-ynyloxy)-3-methoxybenzaldehyde and 3-trifluoromethyl-benzylazide using general procedure; 0.398 g, 0.769 mmol, 97%; mp=130-134° C. (dec.); IR (υ[cm⁻¹]) 3123, 1702, 1689, 1588, 1506, 1329, 1262, 1133, 1123, 994, 792; $^1$H NMR (600 MHz, CDCl$_3$) δ=9.83 (s, 1H), 7.59 (d, J=7.6, 1H), 7.56 (s, 1H), 7.47 (t, J=7.7, 1H), 7.41 (dd, J=15.8, 6.7, 2H), 7.39 (s, 1H), 7.21 (d, J=8.1, 1H), 5.62 (s, 2H), 5.27 (s, 2H), 3.88 (s, 3H); $^{13}$C NMR (151 MHz, CDCl$_3$) δ=191.2, 153.1, 150.5, 147.5, 135.0, 131.6, 131.6 (q, J=32.7), 131.1, 129.9, 126.7, 125.9 (q, J=3.6), 125.1 (q, J=3.7), 123.9 (q, J=272.4), 113.5, 109.7, 81.2, 62.9, 56.3, 54.0; HRMS (ESI-TOF) (m/z): [M+H]$^+$ calcd for C$_{19}$H$_{16}$F$_3$IN$_3$O$_3$, 518.0183; found 518.0186.

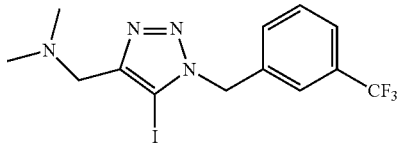 [SMILES: CN(C)Cc1nnn(Cc2cccc(C(F)(F)F)c2)c1I]

1-(5-Iodo-1-(3-(trifluoromethyl)benzyl)-1H-1,2,3-triazol-4-yl)-N,N-dimethylmethanamine (18). Synthesized from 3-iodo-N,N-dimethylpropargylamine and 3-trifluoromethyl-benzylazide using general procedure, sample purified by column chromatography (30:1 CHCl$_3$: MeOH); 0.391 g, 0.953 mmol, 80%; mp=117-119° C. (dec.); IR (υ[cm⁻¹]) 2973, 2827, 1455, 1326, 1164, 1118, 1020, 757; $^1$H NMR (600 MHz, CDCl$_3$) δ=7.57 (d, J=7.7, 1H), 7.52 (s, 1H), 7.45 (t, J=7.7, 1H), 7.39 (d, J=7.7, 1H), 5.63 (s, 2H), 3.54 (s, 2H), 2.29 (s, 6H); $^{13}$C NMR (151 MHz, CDCl$_3$) δ=149.1, 135.5, 131.5 (q, J=32.6), 131.3, 129.9, 125.7 (q, J=3.7), 124.9 (q, J=3.7), 123.9 (q, J=272.5), 81.0, 53.9 (d, J=37.0), 45.3, 30.3; HRMS (ESI-TOF) (m/z): [M+H]$^+$ calcd for C$_{13}$H$_{15}$F$_3$IN$_4$, 411.0288; found 411.0287.

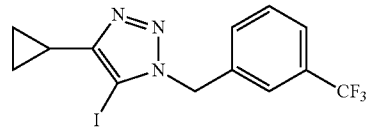 [SMILES: FC(F)(F)c1cccc(Cn2nnc(C3CC3)c2I)c1]

4-Cyclopropyl-5-iodo-1-(3-(trifluoromethyl)benzyl)-1H-1,2,3-triazole (19). Synthesized from (iodoethynyl)cyclopropane and 3-trifluoromethyl-benzylazide using general procedure; 0.589 g, 1.498 mmol, 96%; mp=129-134° C. (dec.); IR (υ[cm⁻¹]) 3087, 3011, 1453, 1325, 1165, 1122, 1074, 777, 701; $^1$H NMR (600 MHz, CDCl$_3$) δ=7.57-7.56 (m, 2H), 7.45 (t, J=7.7, 1H), 7.39 (d, J=7.7, 1H), 5.57 (s, 2H), 1.78-1.72 (m, 1H), 1.06-1.01 (m, 2H), 0.99-0.93 (m, 2H); $^{13}$C NMR (151 MHz, CDCl$_3$) δ=153.8, 135.6, 131.7 (q, J=32.6), 131.4, 129.7, 125.6 (q, J=3.7), 125.0 (q, J=3.9), 124.0 (q, J=272.3), 77.9, 53.7, 7.8, 7.5; HRMS (ESI-TOF) (m/z): [M+Na]$^+$ calcd for C$_{13}$H$_{11}$F$_3$IN$_3$Na, 415.9847; found 415.9847.

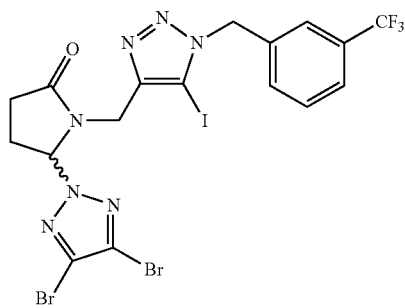 [SMILES: O=C1CCC(n2nc(Br)c(Br)n2)N1Cc1nnn(Cc2cccc(C(F)(F)F)c2)c1I]

5-(4,5-Dibromo-2H-1,2,3-triazol-2-yl)-1-((5-iodo-1-(3-(trifluoromethyl)benzyl)-1H-1,2,3-triazol-4-yl)methyl)pyrrolidin-2-one (20). Synthesized from 5-(4,5-dibromo-2H-1,2,3-triazol-2-yl)-1-(3-iodoprop-2-ynyl)pyrrolidin-2-one and 3-trifluoromethyl-benzylazide using general procedure; 0.663 g, 0.982 mmol, 93%; mp=105-110° C. (dec.); IR (υ[cm⁻¹]) 3002, 2104, 1696, 1415, 1327, 1166, 1123, 1074, 921, 829, 753, 702; $^1$H NMR (600 MHz, CDCl$_3$) δ=7.59 (d, J=7.8, 1H), 7.56 (s, 1H), 7.48 (t, J=7.7, 1H), 7.40 (d, J=7.7, 1H), 6.16 (d, J=7.6, 1H), 5.59 (d, J=3.3, 2H), 4.88 (d, J=15.7, 1H), 3.92 (d, J=15.7, 1H), 2.95-2.86 (m, 1H), 2.65-2.56 (m, 1H), 2.49 (dd, J=17.1, 9.9, 1H), 2.43-2.36 (m, 1H); $^{13}$C NMR (151 MHz, CDCl$_3$) δ=175.0, 147.0, 135.1, 131.6 (m), 131.5, 129.9, 126.1, 125.8 (m), 125.1 (m), 123.9 (m), 79.6, 78.3, 53.9, 36.4, 28.6, 25.6; HRMS (ESI-TOF) (m/z): [M+H]$^+$ calcd for C$_{17}$H$_{14}$Br$_2$F$_3$IN$_7$O, 673.8618; found 673.8613.

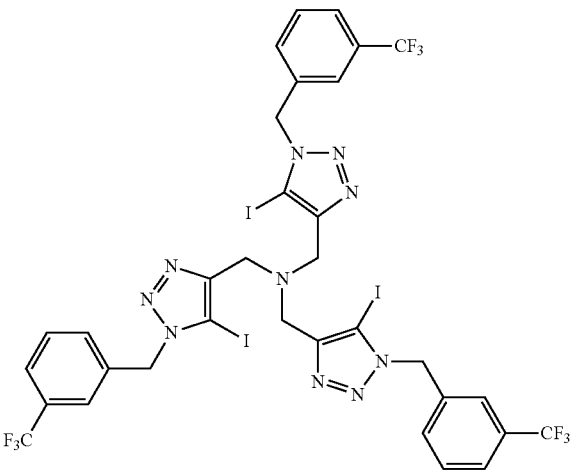 [SMILES: FC(F)(F)c1cccc(Cn2nnc(CN(Cc3nnn(Cc4cccc(C(F)(F)F)c4)c3I)Cc3nnn(Cc4cccc(C(F)(F)F)c4)c3I)c2I)c1]

Tris((5-iodo-1-(3-(trifluoromethyl)benzyl)-1H-1,2,3-triazol-4-yl)methyl)amine (21). Synthesized from tris(3-iodoprop-2-ynyl)amine and 3-trifluoromethyl-benzylazide using general procedure, sample triturated with MeCN; 0.391 g, 0.352 mmol, 81%; mp=171-173° C. (dec.); IR (υ[cm⁻¹]) 3072, 1445, 1328, 1162, 1123, 1095, 756; $^1$H NMR (600 MHz, CDCl$_3$) δ=7.62 (s, 3H), 7.59 (d, J=7.7, 3H), 7.51 (d, J=7.6, 3H), 7.44 (t, J=7.7, 3H), 5.48 (s, 6H), 3.64 (s, 6H); $^{13}$C NMR (151 MHz, CDCl$_3$) δ=149.4, 135.4, 132.3, 131.6 (q, J=32.7), 129.8, 125.9 (q, J=3.6), 125.8 (q, J=3.5), 123.8 (q, J=272.5), 81.2, 53.6, 48.2; HRMS (ESI-TOF) (m/z): [M+H]$^+$ calcd for C$_{33}$H$_{25}$F$_9$I$_3$N$_{10}$, 1112.9249; found 1112.9249.

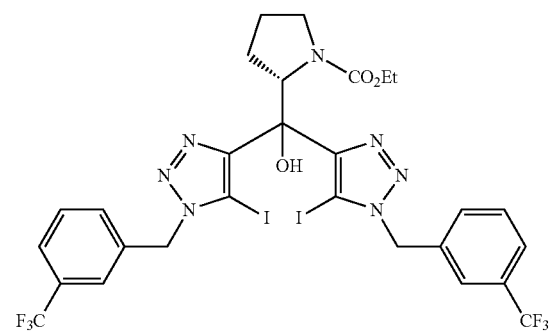 [SMILES: CCOC(=O)N1CCC[C@H]1C(O)(c1nnn(Cc2cccc(C(F)(F)F)c2)c1I)c1nnn(Cc2cccc(C(F)(F)F)c2)c1I]

(S)-Ethyl 2-(hydroxybis(5-iodo-1-(3-(trifluoromethyl)benzyl)-1H-1,2,3-triazol-4-yl)methyl)pyrrolidine-1-carboxylate (22). Synthesized from (5)-ethyl 2-(3-hydroxy-1,5-diiodopenta-1,4-diyn-3-yl)pyrrolidine-1-carboxylate and 3-trifluoromethyl-benzylazide using general procedure, sample purified by column chromatography (2:1 Hex: EtOAc); 0.408 g, 0.466 mmol, 73%; mp=185-189° C. (dec.); IR (υ[cm⁻¹]) 3537, 3075, 2978, 1675, 1453, 1328, 1159, 1111, 1077, 701; ¹H NMR (600 MHz, CDCl₃) δ=7.55 (d, J=5.4, 3H), 7.50-7.36 (m, 5H), 6.60 (br s, 1H, OH), 5.74-5.50 (m, 4H), 5.21 (dd, J=8.5, 4.0, 1H), 4.07 (br s, 2H), 3.46 (br s, 1H), 2.99 (br s, 1H), 2.38 (br s, 1H), 2.35-2.23 (m, J=8.3, 1H), 1.61 (br s, 1H), 1.19 (br s, 3H), 1.13 (br s, 1H); ¹³C NMR (151 MHz, CDCl₃) δ=159.1, 153.2, 150.4, 133.1 (m), 131.5 (m), 129.7, 129.6, 125.6 (m), 125.9 (m), 124.6 (m, J=3.7), 124.2 (m), 79.8, 79.7, 75.6, 65.2, 62.2, 53.8, 53.7, 48.2, 29.0, 23.9, 15.0; HRMS (ESI-TOF) (m/z): [M+H]⁺ calcd for C₂₈H₂₆F₆I₂N₇O₃, 876.0085; found 876.0083.

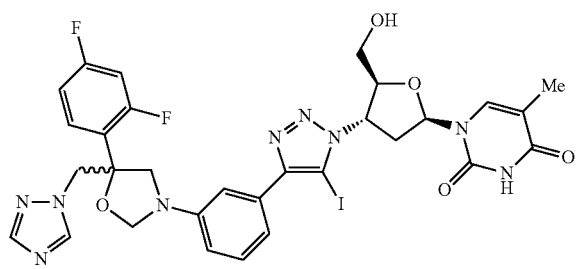 [SMILES: Cc1cn([C@H]2C[C@H](n3nnc(-c4cccc(N5COC(Cn6cncn6)(c6ccc(F)cc6F)C5)c4)c3I)[C@@H](CO)O2)c(=O)[nH]c1=O]

1-((2R,4S,5S)-4-(4-(3-(5-((1H-1,2,4-triazol-1-yl)methyl)-5-(2,4-difluorophenyl)oxazolidin-3-yl)phenyl)-5-iodo-1H-1,2,3-triazol-1-yl)-5-(hydroxymethyl)tetrahydrofuran-2-yl)-5-methylpyrimidine-2,4(1H,3H)-dione (T.O.C. graphic) Synthesized from 5-((1H-1,2,4-triazol-1-yl)methyl)-5-(2,4-difluorophenyl)-3-(3-(iodoethynyl)phenyl)oxazolidine (0.90 g, 1.83 mmol) and azidothymidine (0.49, 1.83 mmol) using general procedure, sample purified by column chromatography (EtOAc-10:1 EtOAc:MeOH) on Biotage KP-NH functionalize silica gel, isolated as a 1:1 mixture of diastereomers; 1.18 g, 1.55 mmol, 85%; mp=201-210° C. (dec.); IR (υ[cm⁻¹]) 3300, 3061, 3011, 2930, 2859, 1686, 1608, 1500, 1473, 1272, 1102, 964, 852, 692; ¹H NMR (600 MHz, CDCl₃) δ=9.76 (s, 1H), 8.08 (s, 1H), 7.75 (s, 1H), 7.47 (s, 1H), 7.36 (dd, J=15.1, 8.6, 1H), 7.31-7.24 (m, 2H), 7.01 (s, 1H), 6.87-6.81 (m, 1H), 6.81-6.76 (m, 1H), 6.52 (d, J=7.6, 1H), 6.34 (t, J=6.8, 1H), 5.55-5.49 (m, 1H), 5.14 (s, 1H), 4.95 (s, 1H), 4.64 (dd, J=76.3, 14.6, 2H), 4.49 (d, J=3.0, 1H), 4.30 (s, 1H), 4.03-3.95 (m, 2H), 3.85 (d, J=10.2, 1H), 3.67 (d, J=9.0, 1H), 3.05-2.96 (m, 1H), 2.96-2.86 (m, 1H), 2.12 (s, 1H), 2.01 (s, 1H), 1.86 (s, 3H); ¹³C NMR (151 MHz, CDCl₃) δ=171.4, 164.2, 164.0 (d, J=12.1), 162.3 (d, J=12.1), 160.0 (d, J=11.8), 158.4 (d, J=11.9), 151.4, 150.8, 150.1, 145.1, 144.6, 138.4, 131.0, 129.8, 128.7-128.2 (m), 123.7-123.4 (m), 118.0, 113.9, 112.6, 111.9 (d, J=21.1), 111.4, 104.8 (t, J=25.9), 89.6, 85.7, 83.2 (d, J=3.6), 81.4, 78.2 (d, J=2.6), 62.3, 60.8, 55.4, 54.7 (d, J=5.3), 37.5, 14.4, 12.7; HRMS (ESI-TOF) (m/z): [M+H]⁺ calcd for C₃₀H₂₈F₂IN₉O₅, 760.1299; found 760.1293.

One-pot/two-step procedure for the synthesis of 5-iodotriazoles using N-iodomorpholine and CuI-TTTA-1-Benzyl-5-iodo-4-p-tolyl-1H-1,2,3-triazole (28): 4-methyl-phenylacetylene (0.5 g, 4.30 mmol) was dissolved in THF (15 ml) and treated with N-iodomorpholine (2.201 g, 6.46 mmol) followed by CuI (0.041 g, 0.215 mmol). Sample was monitored by GC-MS. After 45 min the reaction had gone to completion and a fine white precipitate had formed. The suspension was placed on a pad of neutral alumina (about 25 mL) and the solution was collected under vacuum. The pad was then washed 3 times with THF (4.50 ml) (final volume about 30 mL, including original reaction). This solution was charged with benzyl azide (0.573 g, 4.30 mmol), followed by TTTA (0.092 g, 0.215 mmol) and finally CuI (0.041 g, 0.215 mmol). The reaction was stirred for 3 h, and then the solvent was removed under a stream of compressed air, and the residue was triturated with MeCN/Et₂O. Product was isolated by filtration, giving 28 as a white solid. (1.26 g, 3.36 mmol, 78%).

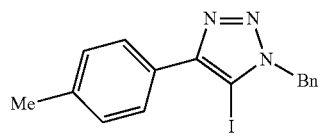 [SMILES: Cc1ccc(-c2nnn(Cc3ccccc3)c2I)cc1]

1-Benzyl-5-iodo-4-p-tolyl-1H-1,2,3-triazole (28). mp=119-120° C. (dec.); IR (υ[cm⁻¹]) 3033, 1541, 1497, 1357, 1229, 1079, 984, 819, 695; ¹H NMR (600 MHz, CDCl₃) δ=7.75 (d, J=8.1, 2H), 7.31-7.26 (m, 3H), 7.25-7.22 (m, 2H), 7.19 (d, J=8.1, 2H), 5.59 (s, 2H), 2.32 (s, 3H); ¹³C NMR (151 MHz, CDCl₃) δ=150.5, 138.7, 134.6, 129.4, 129.1, 128.7, 128.0, 127.5, 76.3, 54.5, 21.6; HRMS (ESI-TOF) (m/z): [M+H]⁺ calcd for C₁₆H₁₅IN₃, 376.0305; found 376.0307.

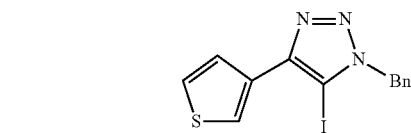 [SMILES: Ic1c(-c2ccsc2)nnn1Cc1ccccc1]

5-Iodo-4-(thiophen-3-yl)-1-benzyl-1H-1,2,3-triazole (29). Synthesized from 3-(iodoethynyl)thiophene and benzylazide using one-pot/two-step general procedure, 1.24 g, 3.38 mmol, 81%; mp=125-127° C. (dec.); IR (υ[cm⁻¹]) 3025, 1496, 1455, 1354, 1318, 1230, 1211, 1072, 1008, 783, 717; ¹H NMR (600 MHz, CDCl₃) δ=7.94 (d, J=1.6, 1H), 7.75 (d, J=4.7, 1H), 7.39 (dd, J=4.7, 3.0, 1H), 7.36-7.29 (m, 3H), 7.29-7.25 (m, 2H), 5.64 (s, 2H); ¹³C NMR (151 MHz, CDCl₃) δ=147.3, 134.5, 131.2, 129.1, 128.7, 127.9, 126.8, 126.1, 122.9, 76.0, 54.5; HRMS (ESI-TOF) (m/z): [M+H]⁺ calcd for C₁₃H₁₁IN₃S, 367.9713; found 367.9713.

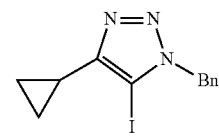 [SMILES: Ic1c(C2CC2)nnn1Cc1ccccc1]

4-Cyclopropyl-5-iodo-1-benzyl-1H-1,2,3-triazole (30). Synthesized from (iodoethynyl)cyclopropane and benzylazide using one-pot/two-step general procedure, 0.843 g, 2.59 mmol, 69%; mp=114-116° C. (dec.); IR (υ[cm⁻¹]) 3028, 1544, 1495, 1451, 1421, 1359, 1333, 1290, 1217, 1145, 1074, 1033, 724; ¹H NMR (600 MHz, CDCl₃) δ=7.31-7.25 (m, 3H), 7.22-7.18 (m, 2H), 5.49 (s, 2H), 1.72 (dq, J=8.4, 5.0, 1H), 1.01-0.97 (m, 2H), 0.91 (ddd, J=10.8, 6.5, 4.1, 2H); ¹³C NMR (151 MHz, CDCl₃) δ=153.4, 134.7, 129.0, 128.5, 127.9, 77.9, 54.2, 7.7, 7.4; HRMS (ESI-TOF) (m/z): [M+H]⁺ calcd for C₁₂H₁₃IN₃, 326.0149; found 326.0151.

One-pot, three-step procedure for the synthesis of 1,4,5-triaryltriazoles-1-(4-methoxyphenyl)-4-phenyl-5-p-tolyl-1H-1,2,3-triazole (31): Phenylacetylene (0.511 g, 5 mmol) was dissolved in THF (20 ml) and treated with N-iodomorpholine (2.56 g, 7.50 mmol) followed by CuI (0.048 g, 0.250 mmol). Sample was stirred for 45 min and monitored by GC-MS. After this time the suspension was poured onto a pad of neutral alumina (about 30 mL) and the solution was collected under vacuum. The pad was then washed 3 times with THF (7.5 ml) (final volume about 42 mL, including original reaction). This solution was charged with 4-methoxyphenylazide (0.746 g, 5.00 mmol), followed by TTTA (0.107 g, 0.250 mmol) and finally CuI (0.048 g, 0.250 mmol). The reaction was stirred for 2 h and monitored by LC-MS. After this time the starting materials had been consumed. The reaction was then charged with p-tolylboronic acid (1.360 g, 10.00 mmol) and TEA (2.108 ml, 15.00 mmol) and then warmed to 65° C. Pd(OAc)$_2$ (0.022 g, 0.100 mmol) was then added and the reaction was stirred for 4 h. After this time the volatile components were removed under vacuum and the residue was purified by column chromatography (4:1 Hex: EtOAc). This gave 31 as a white solid. (1.25 g, 3.65 mmol, 73%).

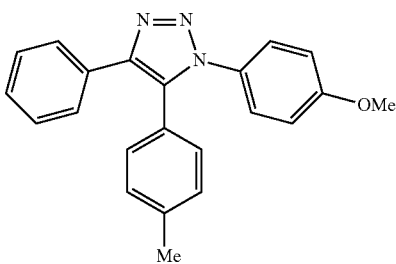 [SMILES: COc1ccc(-n2nnc(-c3ccccc3)c2-c2ccc(C)cc2)cc1]

1-(4-methoxyphenyl)-4-phenyl-5-p-tolyl-1H-1,2,3-triazole (31). mp=162-166° C. (dec.); IR (υ[cm$^{-1}$]) 2967, 1512, 1484, 1253, 1182, 994, 832, 780, 697; $^1$H NMR (600 MHz, CDCl$_3$) δ=7.59 (d, J=7.9, 2H), 7.31-7.25 (m, 3H), 7.21 (d, J=8.6, 2H), 7.09 (dd, J=45.5, 7.6, 4H), 6.85 (d, J=8.6, 2H), 3.80 (s, 3H), 2.35 (s, 3H); $^{13}$C NMR (151 MHz, CDCl$_3$) δ=160.0, 144.6, 139.5, 134.1, 131.3, 130.2, 129.9, 129.9, 128.7, 128.0, 127.5, 126.8, 124.9, 114.4, 55.7, 21.6; HRMS (ESI-TOF) (m/z): [M+H]$^+$ calcd for C$_{22}$H$_{20}$N$_3$O, 342.1601; found 342.1601.

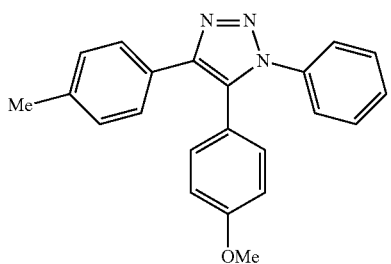 [SMILES: COc1ccc(-c2c(-c3ccc(C)cc3)nnn2-c2ccccc2)cc1]

5-(4-methoxyphenyl)-1-phenyl-4-p-tolyl-1H-1,2,3-triazole (32). Synthesized from 4-methyl-phenylacetylene, phenylazide, N-iodomorpholine and 4-methoxy-phenylboronic acid using one-pot/three-step general procedure, 1.22 g, 3.55 mmol, 71%; mp=172-174° C. (dec.); IR (υ[cm$^{-1}$]) 3064, 2922, 1611, 1523, 1499, 1250, 1177, 995, 847, 820, 760, 687; $^1$H NMR (600 MHz, CDCl$_3$) δ=7.49 (d, J=8.0, 2H), 7.38-7.33 (m, 3H), 7.32-7.27 (m, 2H), 7.10 (dd, J=13.0, 8.2, 4H), 6.85 (d, J=8.5, 2H), 3.80 (s, 3H), 2.32 (s, 3H); $^{13}$C NMR (151 MHz, CDCl$_3$) δ=160.4, 144.9, 137.8, 136.9, 133.4, 131.7, 129.4, 129.3, 129.0, 128.3, 127.4, 125.4, 119.9, 114.7, 55.5, 21.5; HRMS (ESI-TOF) (m/z): [M+H]$^+$ calcd for C$_{22}$H$_{20}$N$_3$O, 342.1601; found 342.1600.

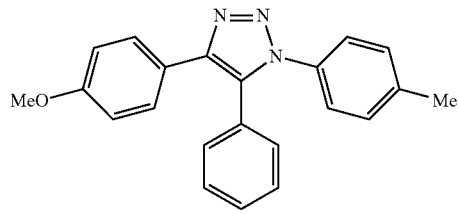 [SMILES: COc1ccc(-c2nnn(-c3ccc(C)cc3)c2-c2ccccc2)cc1]

4-(4-methoxyphenyl)-5-phenyl-1-p-tolyl-1H-1,2,3-triazole (33). Synthesized from 4-methoxy-phenylacetylene, 4-methyl-phenylazide, N-iodomorpholine and phenylboronic acid using one-pot/three-step general procedure, 1.19 g, 3.50 mmol, 70%; mp=192-195° C. (dec.); IR (υ[cm$^{-1}$]) 3019, 2937, 1619, 1517, 1481, 1370, 1247, 1177, 1027, 997, 842, 820, 747; $^1$H NMR (600 MHz, CDCl$_3$) δ=7.50 (d, J=8.4, 2H), 7.39-7.30 (m, 3H), 7.20-7.11 (m, 6H), 6.83 (d, J=8.5, 2H), 3.78 (s, 3H), 2.34 (s, 3H); $^{13}$C NMR (151 MHz, CDCl$_3$) δ=159.5, 144.8, 139.2, 134.3, 133.1, 130.4, 129.9, 129.4, 129.2, 128.8, 128.2, 125.2, 123.6, 114.1, 55.4, 21.4; HRMS (ESI-TOF) (m/z): [M+H]$^+$ calcd for C$_{22}$H$_{20}$N$_3$O, 342.1601; found 342.1605.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. Skilled artisans may employ such variations as appropriate to practice the present invention otherwise than as specifically described herein without departing from the scope of this invention. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method for preparing a 1,2,3-triazole compound comprising contacting an organic azide with a 2-substituted-1-iodoalkyne in the presence of a copper catalyst and an copper-coordinating ligand in a liquid reaction medium, thereby forming a 1,4,5-substituted-1,2,3-triazole compound including a iodo substituent at the 5-position of the triazole, the organic portion of the organic azide at the 1-position of the triazole, and the substituent of the 1-iodoalkyne at the 4-position of the triazole; wherein the copper-coordinating ligand comprises one or more materials selected from the group consisting of an amine, a thiol or salt thereof, a sulfide, a disulfide, a thiophene, a thiazole, and a phosphine.

2. The method of claim 1 wherein the copper catalyst comprises a Cu(I) salt.

3. The method of claim 1 wherein the copper catalyst comprises cuprous iodide.

4. The method of claim 1 wherein the copper catalyst or a portion thereof is generated in situ by reduction of a Cu(II) salt.

5. The method of claim 1 wherein the copper catalyst or a portion thereof is generated in situ by oxidation of Cu(0).

6. The method of claim 1 wherein the copper-coordinating ligand comprises a tertiary amine ligand.

7. The method of claim 1 wherein the copper-coordinating ligand comprises a 1,2,3-triazole-substituted tertiary amine.

8. The method of claim 1 wherein the copper-coordinating ligand comprises triethylamine.

9. The method of claim 1 wherein the copper-coordinating ligand comprises tris((1-tert-butyl-1H-1,2,3-triazolyl)methyl)amine (TTTA) or tris((1-benzyl-1H-1,2,3-triazolyl)methyl)amine (TBTA).

10. The method of claim 1 wherein the liquid reaction medium comprises an aprotic organic solvent.

11. The method of claim 10 wherein the aprotic organic solvent comprises at least one liquid selected from the group consisting of an ether, an amide, a nitrile, a hydrocarbon, and a chlorinated hydrocarbon.

12. The method of claim 1 wherein the liquid reaction medium comprises an alcohol.

13. The method of claim 1 wherein the liquid reaction medium comprises water.

14. The method of claim 1 wherein the organic azide is contacted with at least a stoichiometric amount of the 1-iodoalkyne based on the molar amount of azide in the organic azide and the molar amount of alkyne in the 1-iodoalkyne.

15. The method of claim 1 wherein the organic azide is contacted with less than a stoichiometric amount of the 1-iodoalkyne based on the molar amount of azide in the organic azide and the molar amount of alkyne in the 1-iodoalkyne.

16. The method of claim 1 wherein the organic azide is contacted with greater than a stoichiometric amount of the 1-iodoalkyne based on the molar amount of azide in the organic azide and the molar amount of alkyne in the 1-iodoalkyne.

17. The method of claim 1 including the additional step of separating the 1,4,5-substituted-1,2,3-triazole compound from the copper-coordinating ligand and any copper-containing materials present.

18. The method of claim 1 including the additional step of isolating the 1,4,5-substituted-1,2,3-triazole compound from the liquid reaction medium.

19. The method of claim 1 including the additional step of contacting the 1,4,5-substituted-1,2,3-triazole compound with an arylboronic acid in the presence of a Pd(0) catalyst, thereby replacing the 5-iodo substituent of the triazole with the aryl portion of the arylboronic acid.

20. The method of claim 1 including the additional step of contacting the 1,4,5-substituted-1,2,3-triazole compound with a reducing agent to replace the 5-iodo substituent with a hydrogen.

21. The method of claim 1 wherein the organic azide comprises a polyethylene glycol substituent and the substituent of the 2-substituted-1-iodoalkyne comprises a protein.

22. The method of claim 1 wherein the organic azide comprises a protein substituent and the substituent of the 2-substituted-1-iodoalkyne comprises a polyethylene glycol group.

23. The method of claim 1 wherein the liquid reaction medium includes a reducing agent.

24. The method of claim 23 wherein the reducing agent comprises a thiol compound.

25. The method of claim 24 wherein the thiol compound comprises dithiothreitol (DTT).

26. The method of claim 1 wherein the liquid reaction medium includes a surfactant.

27. The method of claim 26 wherein the surfactant comprises sodium docecyl sulfate.

28. The method of claim 1 wherein the 1,4,5-substituted-1,2,3-triazole compound is represented by the formula

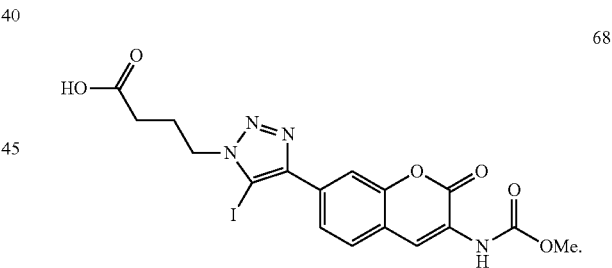

* * * * *